(12) United States Patent
Treacy et al.

(10) Patent No.: US 10,799,335 B2
(45) Date of Patent: Oct. 13, 2020

(54) SOFT TISSUE FIXATION DEVICE

(71) Applicant: Onkos Surgical, Inc., Parsippany, NJ (US)

(72) Inventors: Patrick Treacy, Kinnelon, NJ (US); Jerry D'Alessio, II, Cedar Grove, NJ (US); Jacob Brenza, Montclair, NJ (US)

(73) Assignee: Onkos Surgical, Inc., Parsippany, NJ (US)

(*) Notice: Subject to any disclaimer, the term of this patent is extended or adjusted under 35 U.S.C. 154(b) by 34 days.

(21) Appl. No.: 16/295,650

(22) Filed: Mar. 7, 2019

(65) Prior Publication Data

US 2019/0201184 A1  Jul. 4, 2019

Related U.S. Application Data

(63) Continuation of application No. 15/417,714, filed on Jan. 27, 2017, now Pat. No. 10,251,744.

(51) Int. Cl.
| *A61F 2/08* | (2006.01) |
| *A61F 2/28* | (2006.01) |
| *A61B 17/84* | (2006.01) |
| *A61F 2/38* | (2006.01) |
| *A61F 2/30* | (2006.01) |

(52) U.S. Cl.
CPC .......... *A61F 2/0811* (2013.01); *A61B 17/842* (2013.01); *A61F 2/28* (2013.01); *A61F 2/389* (2013.01); *A61F 2002/0829* (2013.01); *A61F 2002/0858* (2013.01); *A61F 2002/0894* (2013.01); *A61F 2002/2892* (2013.01); *A61F 2002/30011* (2013.01); *A61F 2002/3093* (2013.01); *A61F 2002/30331* (2013.01); *A61F 2002/30433* (2013.01); *A61F 2002/30462* (2013.01); *A61F 2002/30469* (2013.01); *A61F 2002/30487* (2013.01); *A61F 2002/30507* (2013.01); *A61F 2002/30932* (2013.01)

(58) Field of Classification Search
CPC .................. A61F 2/0811; A61F 2/0858; A61F 2002/30011; A61F 2002/30462; A61F 2002/30461; A61F 2002/30469; A61F 2002/0864; A61B 17/82; A61B 17/842; A61B 17/8861

See application file for complete search history.

(56) References Cited

U.S. PATENT DOCUMENTS

| 4,728,335 A | 3/1988 | Jurgutis |
| 4,863,474 A | 9/1989 | Brown et al. |
| 4,883,492 A | 11/1989 | Frey et al. |
| 4,976,738 A | 12/1990 | Frey et al. |

(Continued)

OTHER PUBLICATIONS

International Search Report and Written Opinion Received in PCT/US18/12942 dated Jul. 13, 2018, pp. 13.

(Continued)

*Primary Examiner* — Alvin J Stewart
(74) *Attorney, Agent, or Firm* — Corner Counsel, LLC

(57) ABSTRACT

A device for attaching soft tissue to a prosthetic implant. The device includes a body that includes a frame and a porous section disposed within the frame, wherein the porous section permits the passage of body fluids therethrough to encourage the healing of the soft tissue as well as the growth of soft tissue into and through the porous section.

20 Claims, 20 Drawing Sheets

(56) References Cited

U.S. PATENT DOCUMENTS

| | | | |
|---|---|---|---|
| 5,209,756 | A | 5/1993 | Seedhom et al. |
| 5,376,126 | A * | 12/1994 | Lin .................... A61B 17/746 |
| | | | 623/23.11 |
| D374,287 | S | 10/1996 | Goble et al. |
| 6,056,751 | A | 5/2000 | Fenton, Jr. |
| 6,132,442 | A | 10/2000 | Ferragamo et al. |
| 6,168,596 | B1 | 1/2001 | Wellisz et al. |
| 6,245,110 | B1 | 6/2001 | Grundei et al. |
| 6,371,985 | B1 | 4/2002 | Goldberg |
| 6,383,187 | B2 | 5/2002 | Tormala et al. |
| 6,482,232 | B1 | 11/2002 | Boucher et al. |
| 6,592,622 | B1 | 7/2003 | Ferguson |
| 6,824,566 | B2 | 11/2004 | Kana et al. |
| 6,866,666 | B1 | 3/2005 | Sinnott et al. |
| 7,001,429 | B2 | 2/2006 | Ferguson |
| 7,070,622 | B1 | 7/2006 | Brown et al. |
| 7,175,664 | B1 * | 2/2007 | Lakin .................... A61F 2/36 |
| | | | 623/19.14 |
| 8,118,868 | B2 | 2/2012 | May et al. |
| 8,177,849 | B2 | 5/2012 | Meyers et al. |
| 8,182,542 | B2 | 5/2012 | Ferko |
| 8,226,725 | B2 | 7/2012 | Ferko |
| 8,469,999 | B2 | 6/2013 | Gonzalez-Hernandez |
| 8,579,984 | B2 * | 11/2013 | Borowsky ............ A61B 17/74 |
| | | | 623/19.14 |
| 8,636,800 | B2 | 1/2014 | Ferko et al. |
| 8,690,916 | B2 | 4/2014 | Gonzalez-Hernandez |
| 8,858,634 | B2 | 10/2014 | Lewallen |
| 8,979,940 | B2 | 3/2015 | Porter et al. |
| 9,005,305 | B2 | 4/2015 | Meyers et al. |
| 9,056,012 | B2 | 6/2015 | Crabtree, Jr. et al. |
| 9,278,003 | B2 | 3/2016 | Deffenbaugh et al. |
| 9,289,299 | B2 | 3/2016 | Metzger et al. |
| 9,345,580 | B2 | 5/2016 | Porter et al. |
| 10,251,744 | B2 * | 4/2019 | Treacy ................ A61B 17/842 |
| 2003/0105465 | A1 | 6/2003 | Schmieding et al. |
| 2006/0241776 | A1 | 10/2006 | Brown et al. |
| 2006/0276896 | A1 * | 12/2006 | Fallin .................... A61B 17/80 |
| | | | 623/16.11 |
| 2007/0203499 | A1 | 8/2007 | Boucher et al. |
| 2007/0288020 | A1 * | 12/2007 | Yang .................... A61F 2/0811 |
| | | | 606/279 |
| 2008/0255622 | A1 | 10/2008 | Mickiewicz et al. |
| 2008/0269894 | A1 * | 10/2008 | Melvin ................ A61F 2/0811 |
| | | | 623/13.14 |
| 2008/0281428 | A1 * | 11/2008 | Meyers ................ A61F 2/389 |
| | | | 623/20.35 |
| 2010/0131069 | A1 | 5/2010 | Halbrecht |
| 2010/0286778 | A1 * | 11/2010 | Eisermann ............ A61F 2/442 |
| | | | 623/17.11 |
| 2010/0298947 | A1 | 11/2010 | Unger |
| 2011/0009973 | A1 * | 1/2011 | Meyers ................ A61F 2/3607 |
| | | | 623/20.32 |
| 2011/0054625 | A1 | 3/2011 | Ferko et al. |
| 2011/0130840 | A1 * | 6/2011 | Oskouei .............. A61F 2/30721 |
| | | | 623/18.11 |
| 2011/0288565 | A1 * | 11/2011 | Kubiak .............. A61B 17/1146 |
| | | | 606/151 |
| 2013/0030529 | A1 * | 1/2013 | Hunt .................... A61F 2/447 |
| | | | 623/16.11 |
| 2013/0030540 | A1 * | 1/2013 | Leibinger .................. A61F 2/28 |
| | | | 623/20.32 |
| 2016/0100835 | A1 * | 4/2016 | Linder .................. A61B 17/08 |
| | | | 606/220 |
| 2017/0156847 | A1 * | 6/2017 | Ricci .................. A61B 17/1146 |
| 2018/0214261 | A1 * | 8/2018 | Treacy .................. A61F 2/0811 |
| 2019/0201184 | A1 * | 7/2019 | Treacy .................... A61F 2/389 |
| 2019/0307549 | A1 * | 10/2019 | Esformes .............. A61F 2/0077 |
| 2020/0085563 | A1 * | 3/2020 | D'Agostino .............. A61F 2/34 |

OTHER PUBLICATIONS

Invitation to Pay Additional Fees And, Where Applicable, Protest Fee received in PCT/US18/12942 dated May 9, 2018; pp. 3.

* cited by examiner

SOFT TISSUE FIXATION DEVICE

CROSS-REFERENCE TO RELATED APPLICATIONS

This application is a continuation of U.S. patent application Ser. No. 15/417,714, published as U.S. Patent Application Publication No. 2018/0214261, filed Jan. 27, 2017.

FIELD OF THE INVENTION

The present disclosure relates to a device for the retention of soft tissue. More specifically, the present disclosure relates to a device for attaching soft tissue to a bone replacement device, such as to a proximal tibial implant.

DESCRIPTION OF THE PRIOR ART

When replacing a joint in a patient, it is preferable to maintain connection of as much of the soft tissue as possible while replacing the articulation surfaces of the bones, thereby preserving the flexor and extensor mechanisms of the joint. However, preservation of the soft tissue connections is not always possible. This may occur, for example, in the case of oncological bone disease, revision surgery with significant bone loss, or a traumatic injury that requires resection and prosthetic reconstruction of the attachment points.

Resection of the portion of the bone that includes the soft tissue attachment points leaves the surgeon with the dilemma of attaching the soft tissue to the prosthesis. Mechanical attachment of soft tissue to the prosthesis is often accomplished via sutures or a clamp. However, in order to achieve long term success, the ultimate goal is for there to be biological fixation of the soft tissue to the prosthesis.

A technique currently utilized to achieve biological fixation of a patellar tendon to a proximal tibial implant is to first mechanically attach the tendon to the prosthesis with either sutures or a mechanical device such as a clamp, and then cover the reconstruction with a medial or lateral gastrocnemius flap over the top of the remnant of the patellar tendon and prosthesis. The gastrocnemius flap provides a soft tissue closure under the skin and also provides additional blood supply to the tendon. This additional blood supply can thereby promote tissue growth of the patellar tendon and biological fixation of the patellar tendon to a surface of the proximal tibial implant. Similar techniques are currently utilized to achieve biological fixation of tendons, or muscles, or other soft tissues to prostheses in other joints, such as the proximal femur and the shoulder. When performing these surgical techniques, the use of sutures to attach the tendon to the prosthesis has several downfalls. First, the sutures have minimal purchase in the tendon and can cause the tendon to tear at the points of contact, allowing the tendon to pull away from the prosthesis, making biological fixation difficult. Second, the process of attaching sutures is time consuming, and therefore, inefficient for the surgeon. Third, the construct is initially only as strong as the rupture strength of the suture. The use of a mechanical device such as a clamp to attach the tendon to the prosthesis alleviates these issues. However, presently available clamps, while providing a larger purchase area, also prevent the healing factors provided by the gastrocnemius flap from reaching the portions of the tendon under the clamps, thereby reducing the likelihood of biological fixation. The present disclosure provides a time-saving soft tissue fixation device that enables a large, secure mechanical attachment, and allows the healing factors to reach the entire portion of the tendon that is in contact with the prosthesis, thereby maximizing the likelihood of achieving biological fixation of the tendon to the prosthesis.

SUMMARY OF THE INVENTION

The present disclosure provides devices and methods for fixation of soft tissue to prosthetic implants. The soft tissues may include, but are not limited to, ligaments, tendons, and/or muscles. The prosthetic implants may include prostheses for replacing all or a portion of any bone adjacent to a joint.

According to one exemplary embodiment, the soft tissue fixation device includes a body with an anterior surface, a posterior surface, and a depth extending from the anterior surface to the posterior surface. The body also includes a distal end, a proximal end, and a height extending from the distal end to the proximal end, as well as a lateral end, a medial end, and a width extending from the lateral end to the medial end. The posterior surface of the soft tissue fixation device has a concave portion that generally matches a convex portion of an anterior surface of a prosthetic implant. The body of the soft tissue fixation device also includes a frame with a solid perimeter and a porous section disposed within the solid perimeter of the frame. The porous section extends through the depth of the body so the anterior surface is in communication with the posterior surface through the porous section. The porous section extends across a majority of the height and width of the body of the soft tissue fixation device.

The soft tissue fixation device may be secured to the prosthetic implant using one of several securing structures. The securing structures may include medial and lateral attachment openings extending from the anterior surface to the posterior surface and a cable configured to first pass through one of the openings and a corresponding lateral or medial channel in the prosthetic implant extending from an anterior surface to a posterior surface of the prosthetic implant. The cable is configured to then be passed through the other channel and attachment opening. The trailing end of the cable includes a protrusion that is larger than the openings. The device also includes a crimp configured to be attached to the cable adjacent to the lateral or medial opening the cable exits, wherein the crimp is larger than the opening.

The securing structures may also include medial and lateral attachment posts with flat surfaces for engagement with medial and lateral set screws. The attachment posts extend from the posterior surface proximate the medial and lateral ends. The medial and lateral attachment posts are configured to fit within medial and lateral attachment openings in the prosthetic implant. It should be noted that the device may be symmetrical, enabling the posts to be interchangeably utilized in either opening, or the device may be asymmetrical.

Another exemplary embodiment discloses a tibial orthopedic implant including a proximal tibial component and a soft tissue attachment device. The proximal tibial component is configured to attach to and extend from a resected proximal tibia. The proximal tibial component includes a body having an anterior surface, a posterior surface, a medial side, a lateral side, a distal end, and a proximal end. The anterior surface includes a porous section configured to allow tissue ingrowth. The porous section has a convex curvature extending from proximate the medial side to proximate the lateral side. The body also includes a plurality of openings adjacent the porous section. The proximal tibial component also includes an articulation component configured to attach to the proximal end of the body and includes a bearing surface configured to bear against a distal femoral implant. The implant also includes a soft tissue attachment device that has an anterior surface, a posterior surface, and a depth extending from the anterior surface to the posterior surface. The soft tissue attachment device also has a distal end, a proximal end, and a height extending from the distal end to the proximal end, and a lateral end, a medial end, and a width extending from the lateral end to the medial end. The posterior surface of the soft tissue attachment device has a concave portion that generally matches the convex curvature of the porous section of the body of the proximal tibial component. The soft tissue attachment device further includes a frame with a solid perimeter and a porous section disposed within the solid perimeter. The porous section extends through the depth of the soft tissue attachment device so the anterior surface is in communication with the posterior surface through the porous section. Also, the porous section extends across a majority of the height and width of the soft tissue attachment device.

These and other objects of the present invention will be apparent from review of the following specification and the accompanying drawings.

BRIEF DESCRIPTION OF THE DRAWINGS

The accompanying drawings, which are incorporated in and constitute a part of the specification, illustrate preferred embodiments of the invention and, together with the description, serve to explain the objects, advantages, and principles of the invention.

DETAILED DESCRIPTION OF THE PREFERRED EMBODIMENT

Figure 1A:
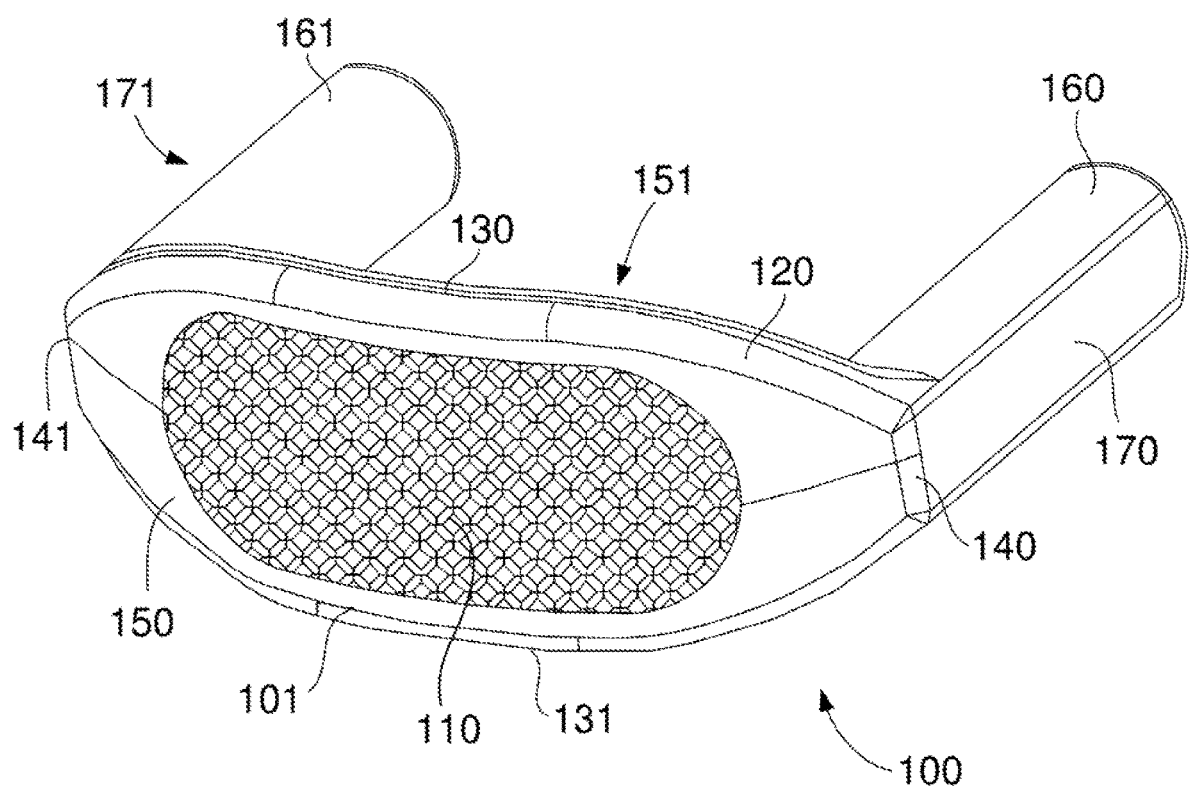
FIG. 1A is a perspective view of a soft tissue attachment device in accordance with an exemplary embodiment of the present invention.
Figure 1B:
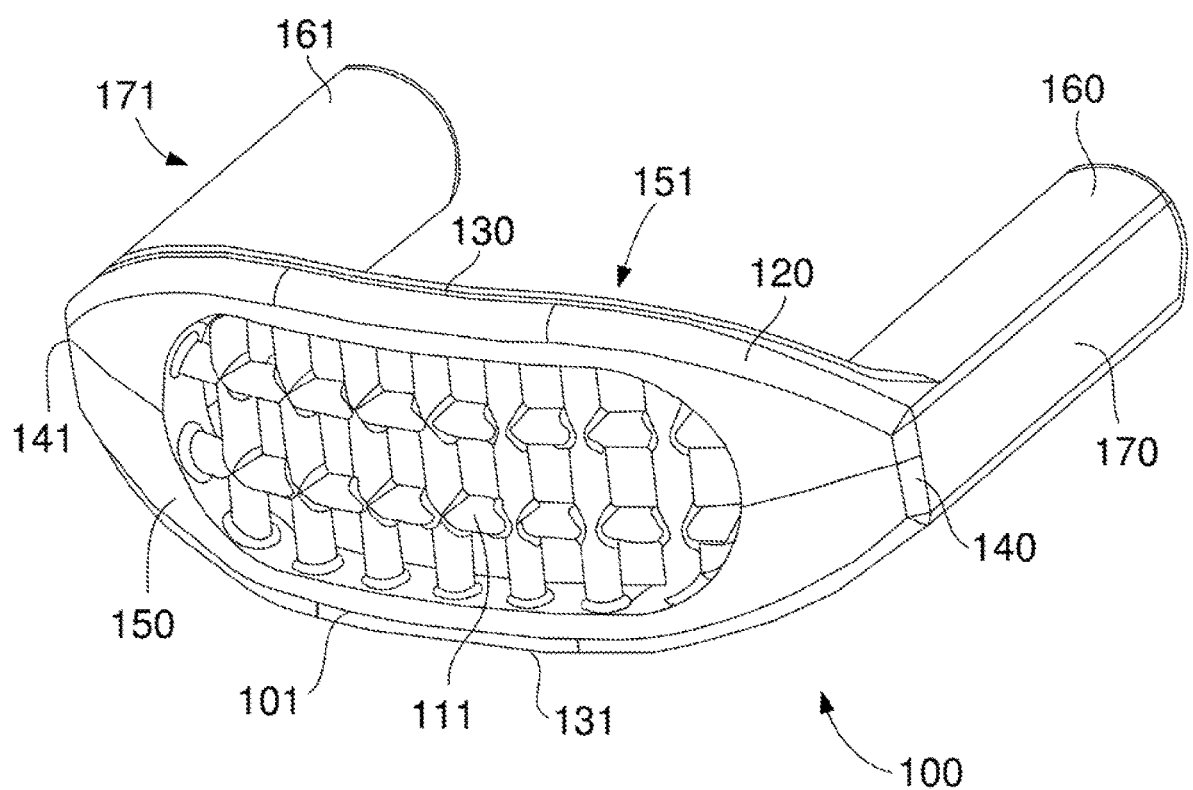
FIG. 1B is a perspective view of a soft tissue device in accordance with another exemplary embodiment of the present invention.
Figure 2:
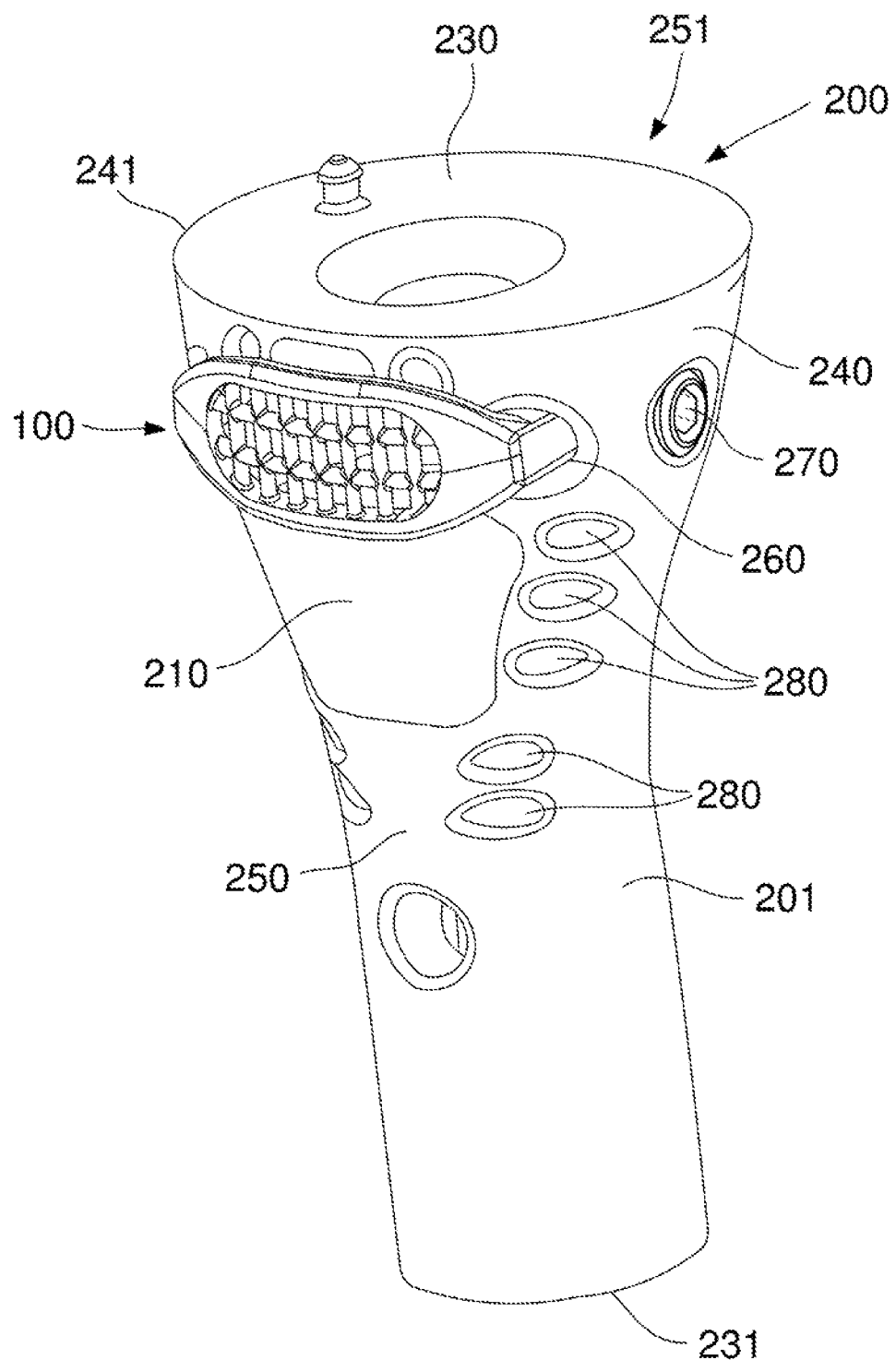
FIG. 2 is a perspective view of the soft tissue attachment device in FIG. 1A in combination with a proximal tibial component in accordance with an exemplary embodiment of the present invention.
Figure 3:
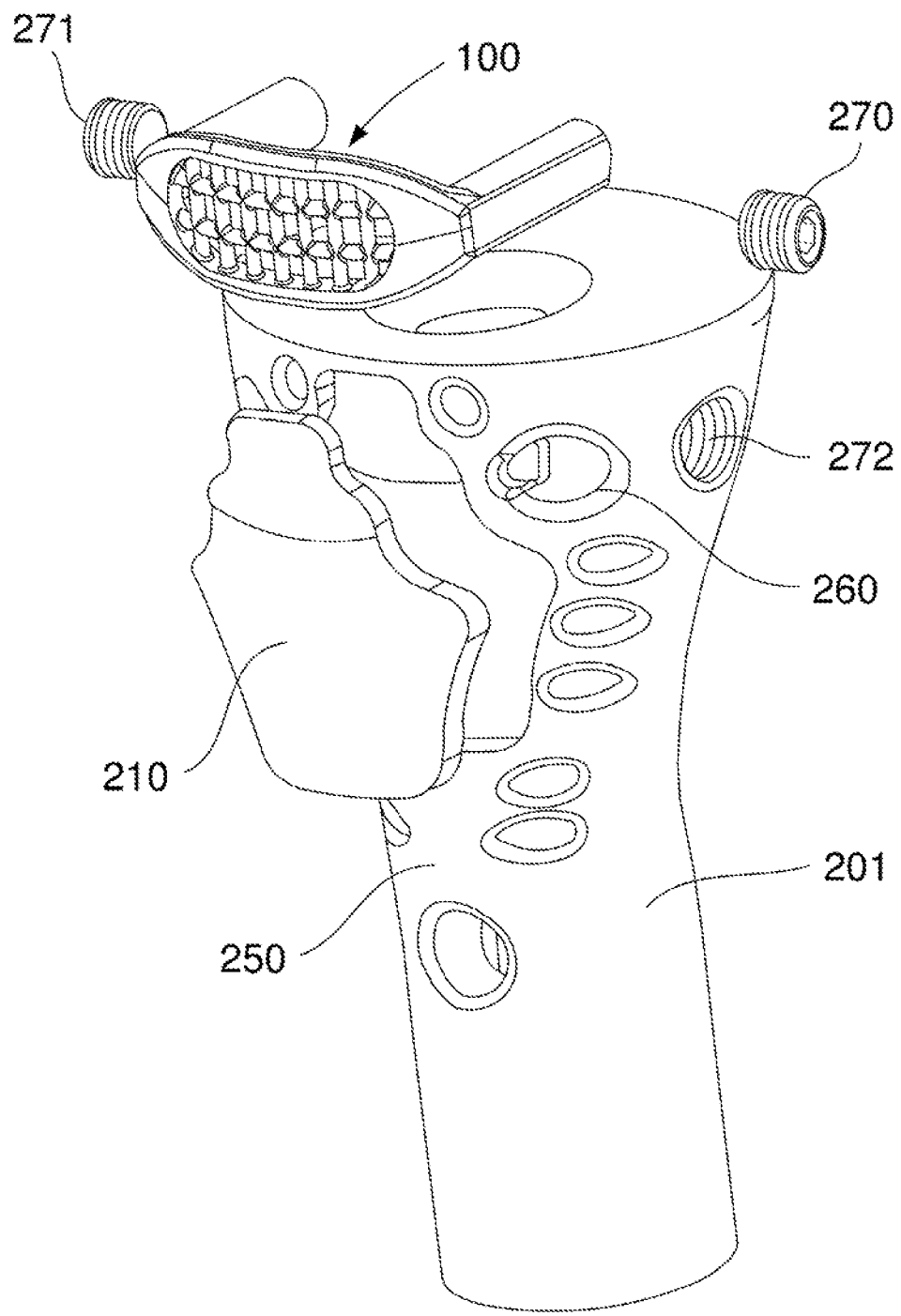
FIG. 3 is an exploded perspective view of the embodiment of FIG. 2.
Figure 4:
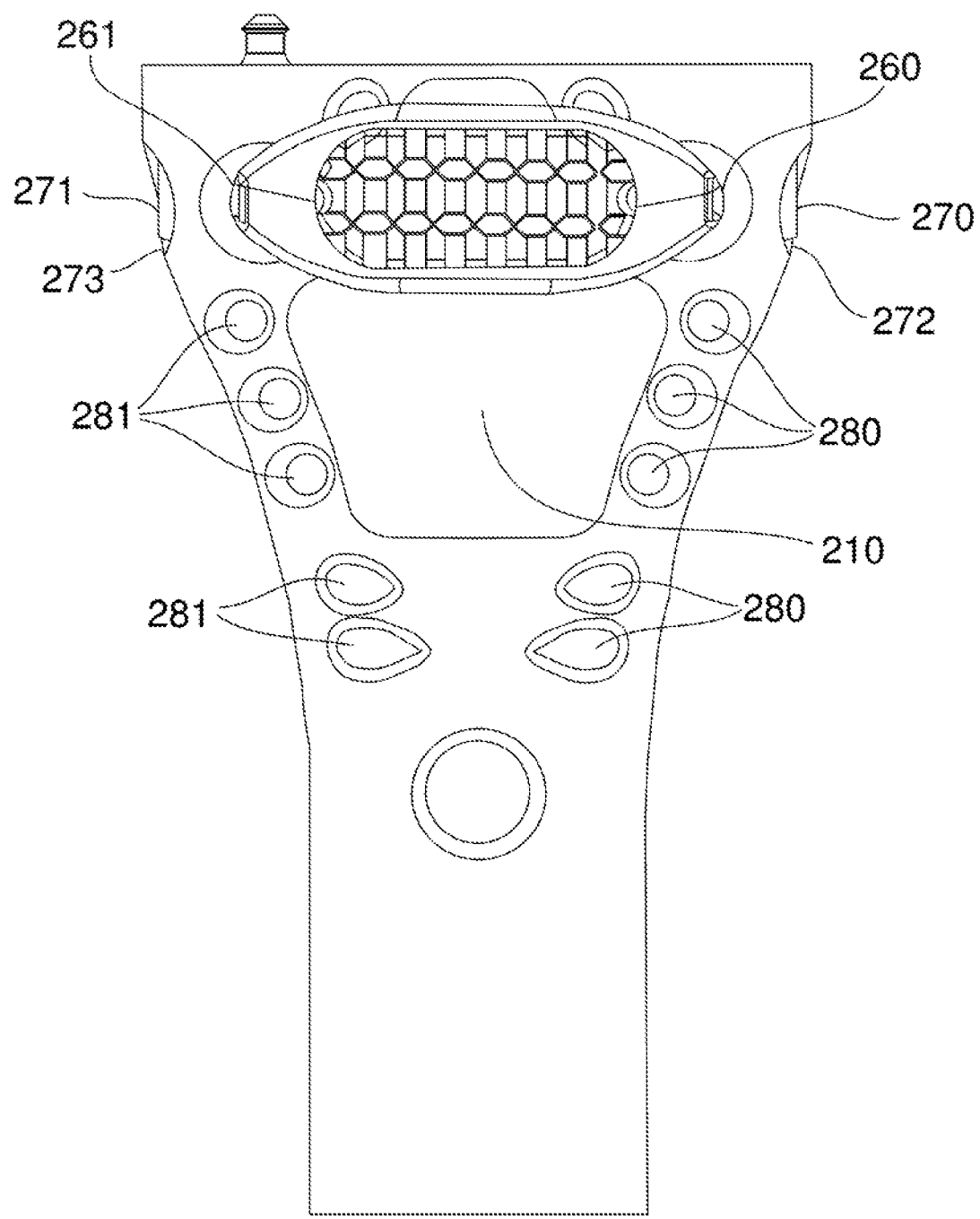
FIG. 4 is a front elevation view of the embodiment of FIG. 2.
Figure 5:
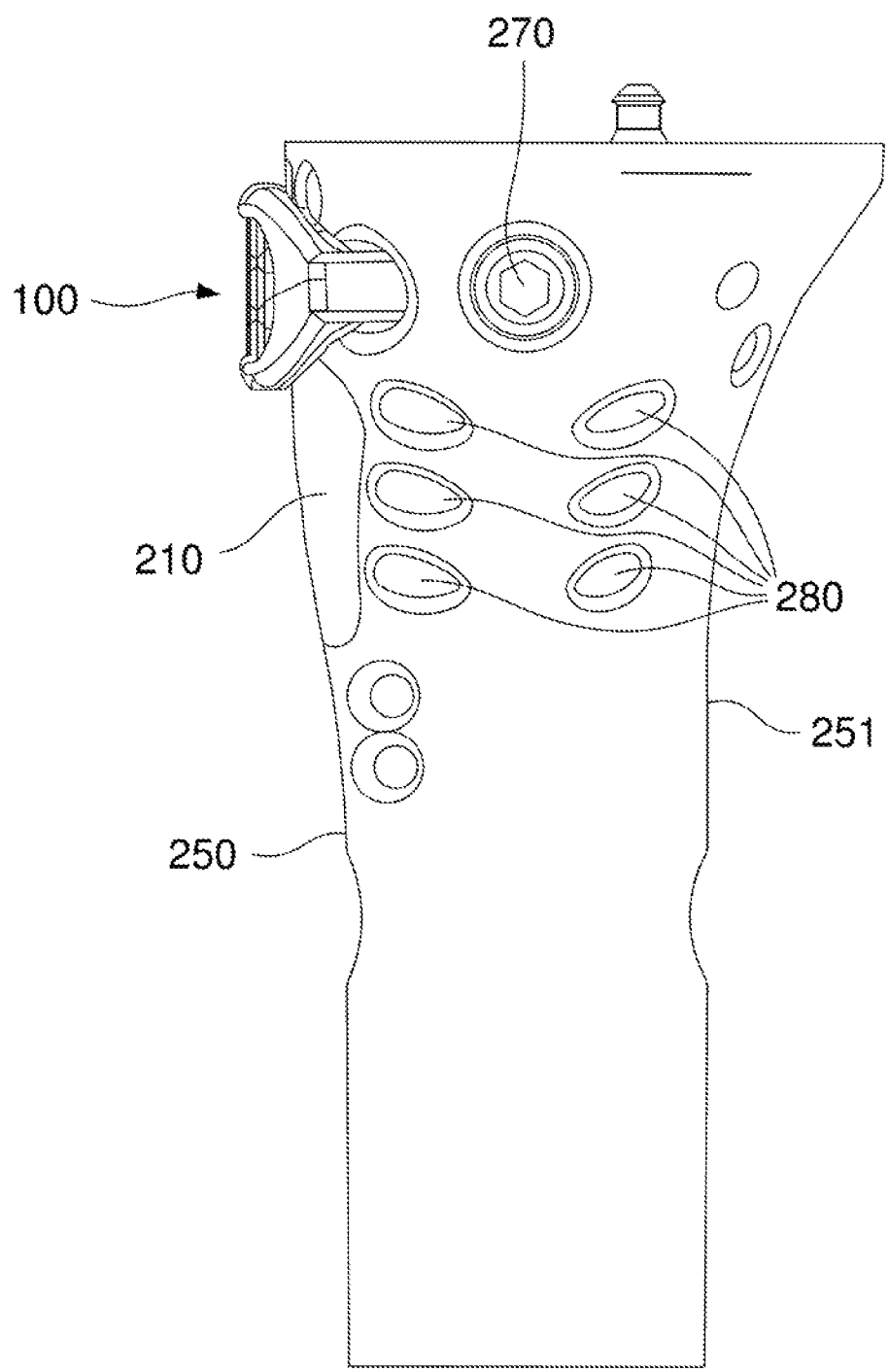
FIG. 5 is a side elevation view of the embodiment of FIG. 2.

The detailed description of the invention, below, is described, and shown in the figures, for use with a proximal tibial component. However, it should be understood that the invention could be used for securing any soft tissue to any implant or joint replacement device in a patient.

Referring to FIGS. 1-5, soft tissue attachment device 100 is used to mechanically attach a patellar tendon of a patient to proximal tibial component 200 while allowing blood and other joint fluids to reach the mechanically attached tendon after the soft tissue attachment device is secured to encourage biological fixation of the tendon to tibial component 200. Further, the clamp will allow for soft tissue fixation or ingrowth in a similar fashion to that of the tibial component 200. Device 100 includes body 101 which includes two parts, frame 120 and porous section 110. Frame 120 and porous section 110 may be made of a single material, such as titanium, stainless steel, tantalum, cobalt-chrome, tungsten or any other biocompatible material, or compound material, such as for example titanium coated PEEK, suitable for human implantation. If porous section 110 and frame 120 are made of the same type of material, then it is preferred, although not necessary, that they are unitary for enhanced structural purposes. Alternatively, porous section 110 and frame 120 may be made of different materials. Porous section 110 may be made of any porous material that will readily permit the passage of bodily fluids or soft tissue therethrough, including ceramics, metals, polymers, and combinations thereof. Furthermore, porous section 110 may be formed of lattice 111 made of horizontally and vertically aligned strips, or strips in any other orientation, having wide or narrow spacing. Alternatively, lattice 111 may serve as a support structure for another porous material that covers and is attached to lattice 111. In this configuration, the horizontal and vertical strips are used more for structural support, as the porous section is optimized for soft tissue ingrowth. The porous structure can be created from standard geometric shapes such as dodecahedrons or octahedrons that are stacked to create a pore size between 500-700 microns and a porosity of 60-80%. This configuration can be ordered or randomized. The preferred pore size mentioned can be optimized for allowing soft tissue to grow into the construct to provide viable long term biologic fixation. Further, by having the porous structure on the clamp, the tissue can also infiltrate the clamp and the underlying prosthetic tibia. Additionally, the porosity and structure can be optimized for bone or hard tissue ingrowth for the tibia or other replacement joints.

Body 101 of device 100 includes anterior surface 150, posterior surface 151, and a depth between anterior surface 150 and posterior surface 151. Anterior surface 150 and posterior surface 151 are in communication through porous section 110. Posterior surface 151 is configured to contact and retain the patellar tendon against tibial component 200. Retention is accomplished by a clamping force applied to the tendon between device 100 and tibial component 200. However, applying excessive force to ensure retention can prevent blood flow to the tendon causing necrosis of the tendon, and therefore, preventing the desired biological fixation. Accordingly, posterior surface 151 may include a friction enhancing surface to increase mechanical retention under less clamping force. The friction enhancing surface may include a roughened surface, barbs, teeth, or any other structure suitable to aid retention.

Body 101 of device 100 further includes distal end 131, proximal end 130, and a height extending between distal end 131 and proximal end 130. Body 101 also includes lateral end 140, medial end 141, and a width extending between lateral end 140 and medial end 141. Posterior surface 151 of body 101 may be, at least in part, concave along the width of body 101, and anterior surface 150 may be convex along the width of body 101. As will be appreciated, the use of the terms medial and lateral to describe the embodiments show in the figures describes an implant for the left knee of a patient. The use of these terms, as well as any other directional terms used throughout the specification and claims, which are well known to those skilled in the art, is merely for convenience, and the terms should be considered interchangeable in the context of relative special relationships and other parts of a human body.

Device 100 may include lateral attachment post 160 extending from posterior surface 151, proximate lateral end 140. Lateral attachment post 160 includes flat surface 170 along at least a portion of a length thereof for engagement with lateral set screw 270. Device 100 may further include medial attachment post 161 extending from posterior surface 151, proximate medial end 141. Medial attachment post 161 includes flat surface 171 along at least a portion of a length thereof for engagement with lateral set screw 271. While affixing device 100 to tibial component 200 using set screws 270 and 271, the surgeon should apply and maintain the desired clamping force while tightening set screws 270 and 271.

Referring to FIGS. 2-5, proximal tibial component 200 is configured to be attached to, and extend proximally from, a resected proximal tibia of a patient. Tibial component 200 includes a body 201 with anterior surface 250, posterior surface 251, lateral side 240, medial side 241, proximal end 230, and distal end 231. Anterior surface 250 includes a porous section 210. Porous section 210 is generally in the desired location for the patellar tendon to achieve biological fixation. Porous section 210 is made of material that permits ingrowth of soft tissue. Porous section 210 can be created from standard geometric shapes such as dodecahedrons or octahedrons that are stacked to create a pore size between 500-700 microns and a porosity of 60-80%. This configuration can be ordered or randomized. The preferred pore size mentioned is optimized for allowing soft tissue to grow into the construct to provide viable long term biologic fixation. Additionally, the porosity and structure can be optimized for bone or hard tissue ingrowth for the tibia or other replacement joints. Porous section 210 may be manufactured separately from body 201 and then mechanically attached to body 201 using mechanical fasteners or by any other means known to those skilled in the art (not shown). If porous section 210 is manufactured separately from body 201, porous section 210 may be made of a different material than body 201. When manufactured separately, porous section 210 may be made of any ceramics, metals, polymers, or combinations thereof having suitable porosity to permit tissue ingrowth and structural integrity to serve as the anchor point of the extensor mechanism of the leg. However, preferably, the solid body 201 and porous section 210 are manufactured as a unitary structure utilizing three-dimensional printing technology, which is well known in the art. If body 201 and porous section 210 are a unitary structure, they may be made of titanium, stainless steel, tantalum, cobalt chrome, tungsten or any other biocompatible material or combination thereof suitable for human implantation having the structural strength to carry the loads required of a prosthetic knee.

Body 201 of tibial component 200 further includes lateral attachment opening 260 configured to receive lateral attachment post 160 therein. Lateral attachment opening 260 is in communication with threaded lateral set screw opening 272 to facilitate the engagement of lateral set screw 270 with flat surface 170 on lateral attachment post 160. Body 201 also includes medial attachment opening 261 configured to receive medial attachment post 161 therein. Medial attachment opening 261 is in communication with threaded medial set screw opening 273 to facilitate the engagement of medial set screw 271 with flat surface 171 on medial attachment post 161. Body 201 may also include a second pair of lateral and medial attachment openings 260, 261 and lateral and medial set screw openings 272, 273 distal of the first pair to facilitate the use of a second soft tissue attachment device 100.

Body 201 may further include a plurality of lateral openings 280 and a plurality of medial openings 281 to facilitate attachment of soft tissue, such as either the patellar tendon or the gastrocnemius flap, via sutures to tibial component 200. Alternatively, body 201 may include additional structure to permit the use of addition soft tissue attachment devices to retain the desired soft tissues, such as the gastrocnemius flap.

Proximal tibial component 200 further includes an articulation component (not shown) configured to attach to proximal end 230. The articulation component includes a bearing surface configured to bear against a distal femur or a distal femoral implant (not shown).

Figure 6:
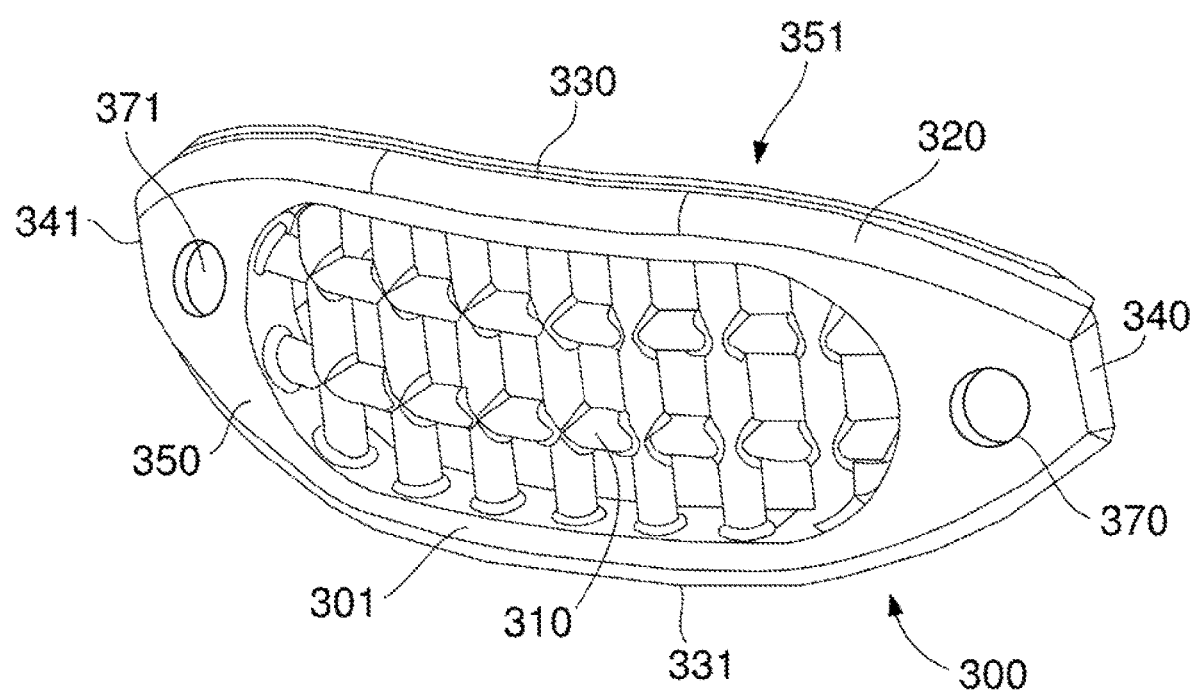
FIG. 6 is a perspective view of a soft tissue attachment device in accordance with another exemplary embodiment of the present invention.
Figure 7:
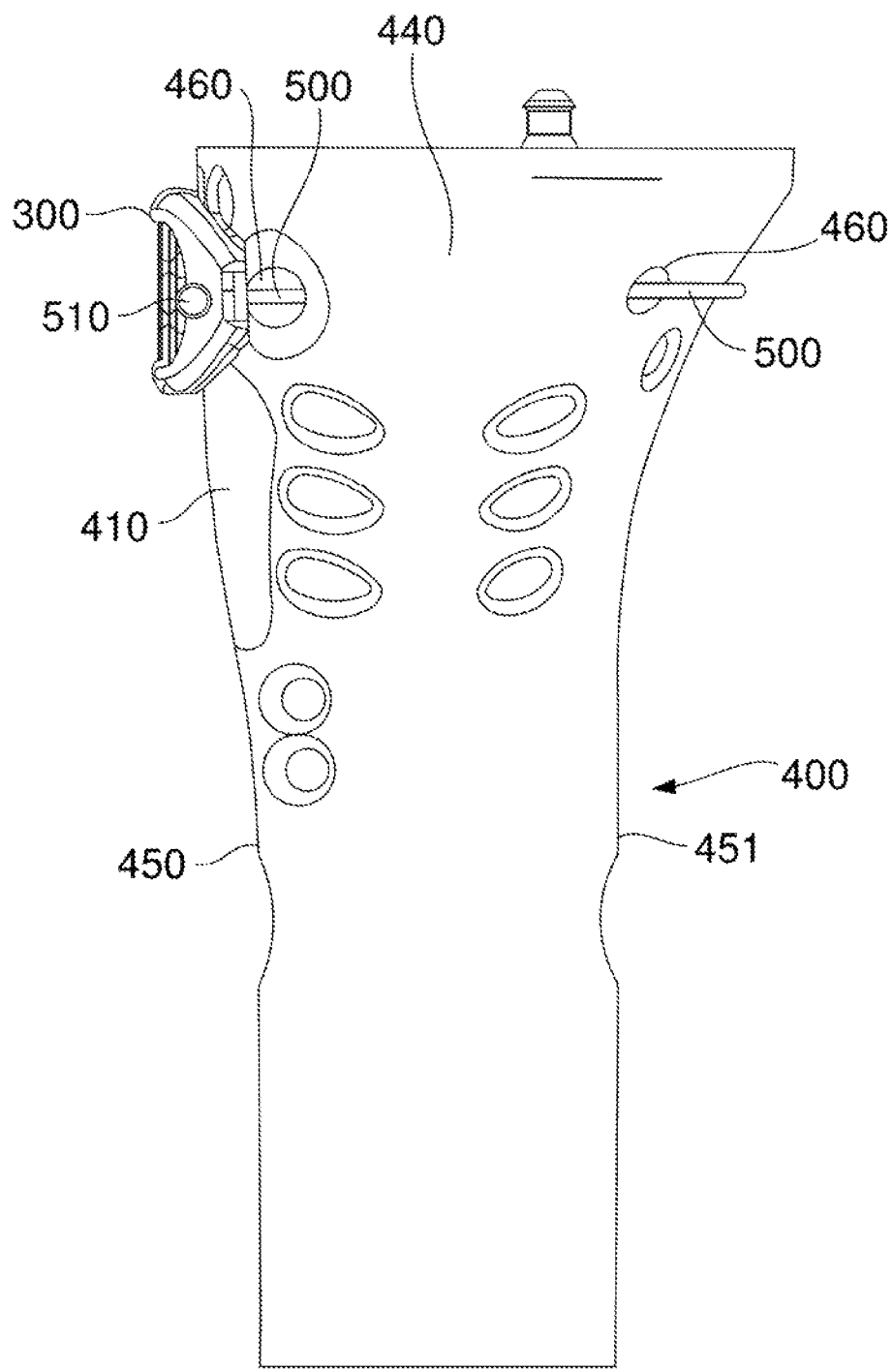
FIG. 7 is a side elevation view of the soft tissue attachment device in of FIG. 6 in combination with a proximal tibial component in accordance with another exemplary embodiment of the present invention.

FIGS. 6-7 show soft tissue attachment device 300. Device 300 is similar to device 100 except for the apparatus used to attach device 300 to proximal tibial component 400. Similar to device 100, device 300 includes body 301 which has two parts, frame 320 and porous section 310. Body 301 of device 300 includes anterior surface 350, posterior surface 351, distal end 331, proximal end 330, lateral end 340, and medial end 341. Body 301 includes lateral attachment opening 370 which extends from anterior surface 350 to posterior surface 351 and is located proximate lateral end 340. Body 301 also includes medial attachment opening 371 which extends from anterior surface 350 to posterior surface 351 and is located proximate medial end 341. It should be noted that device 300 may include medial and lateral posts (not shown) similar to 170 and 171 of device 100. The medial and lateral posts of device 300 are utilized to properly align and stabilize device 300 relative to the prosthesis. In the embodiment including medial and lateral posts, the lateral and medial openings 370, 371 extend longitudinally through the posts.

Attachment of device 300 is facilitated by cable 500. Cable 500 may be made of a woven polymeric material or a monofilament wire. Cable 500 includes protrusion 510 attached to a trailing end of cable 500. Protrusion 510 may be spherical, cylindrical, or conical. Protrusion 510 has a larger maximum dimension than lateral attachment opening 370 so as to prevent protrusion 510 from passing through opening 370. Lateral attachment opening 370 may be countersunk so that a trailing end of protrusion 510 is flush with anterior surface 350 when installed. A leading end of cable 500 is secured by a cable retention device (not shown) affixed to cable 500 adjacent to medial attachment opening 371. The cable retention device may be spherical, cylindrical, or conical shape. The cable retention device has a maximum dimension larger than medial attachment opening 371 so as to prevent the cable retention device from passing through opening 371. The cable retention device may be a crimp which is constructed of a plastically deformable material, wherein the crimp is affixed to cable 500 by the application of sufficient pressure to permanently deform the crimp around cable 500. The deformable crimp may have a slot on a side to permit the crimp to slide laterally onto cable 500, or the crimp may have a central thru-hole permitting the crimp to be axially introduced on to cable 500 prior to deformation. Alternatively, the cable retention device may be constructed of a rigid material and include a thru-hole. The thru-hole includes back-angled teeth that permit the cable retention device to travel along cable 500 from the leading end toward the trailing end, but prohibit movement from the trailing end toward the leading end. In yet a further alternative, the retention device may have a set screw hole in communication with the thru-hole, thereby permitting the introduction of a set screw for the retention of the cable with respect to the cable retention device. In yet a further alternative, a crimped component can be used to secure to cable 500 and prevent movement with the soft tissue attachment device by mating with opening 370 or 371. Medial attachment opening 371 may be countersunk so that a trailing end of the cable retention device is flush with anterior surface 350 when installed.

FIG. 7 shows proximal tibial component 400 with device 300 attached thereto. Proximal tibial component 400 is similar to proximal tibial component 200. However, tibial component 400 need not include set screw holes. Tibial component 400 includes a body 401 with anterior surface 450, posterior surface 451, lateral side 440, and a medial side (not shown). Anterior surface 450 includes a porous section 410. Body 401 of tibial component 400 further includes lateral attachment channel 460 which extends from anterior surface 450 to posterior surface 451 proximate lateral side 440 and is configured to receive cable 500 therethrough. Body 401 of tibial component 400 also includes a medial attachment channel (not shown) which extends from anterior surface 450 to posterior surface 451 proximate the medial side and is configured to receive cable 500 therethrough. Cable 500 is configured to be inserted first through lateral attachment opening 370 then through corresponding lateral attachment channel 460. After exiting lateral attachment channel 460, cable 500 is wrapped around posterior surface 451 and is passed through the medial attachment channel and medial attachment opening 371. After the leading end of cable 500 exits medial attachment opening 371, sufficient tension is applied to cable 500 to generate enough force between device 300 and tibial component 400 to retain the patellar tendon. The correct cable tension is then maintained by affixing the cable retention device to cable 500. Alternatively, body 401 may include a groove (not shown) extending from lateral attachment channel 460 to the medial attachment channel along posterior surface 451. The groove should have a width and depth roughly equal to the diameter of cable 500 so that when installed, cable 500 is flush with posterior surface 451. In another alternative, lateral attachment channel 460 does not exit posterior surface 451, and instead, curves around inside body 401 and connects to the medial attachment channel, thereby forming one continuous channel beginning and ending on anterior surface 450. In a further alternative, proximal tibial component 400 and device 300 may be configured to accept multiple cables 500 therethrough, including having the cables inserted from opposite directions.

FIGS. 8-18 show various different structures that may be utilized to affix a soft tissue attachment device to a prosthesis. For clarity purposes, the prostheses are omitted from the figures. However, one of ordinary skill in the art would understand the corresponding structure required in the prostheses to accommodate the depicted structures. While not shown in the figures, it should be understood that the embodiments shown in FIGS. 8-18 may include a porous section. Also not shown in the figures is the tibial component.

Figure 8:
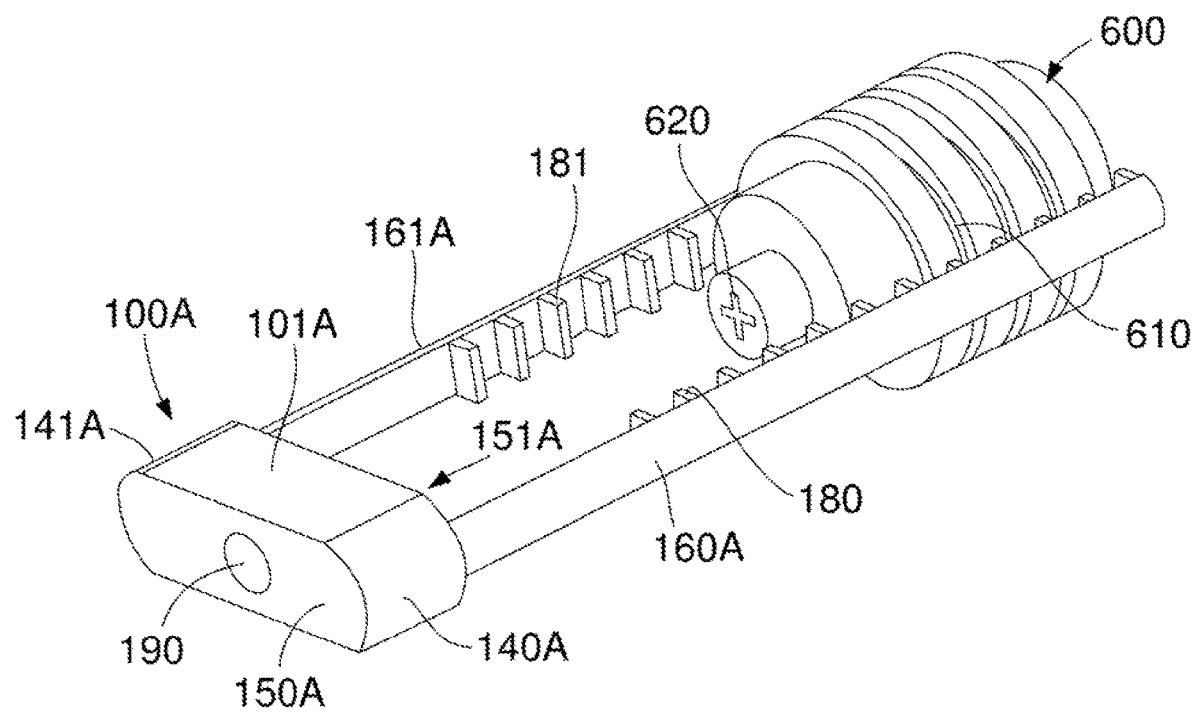
FIG. 8 is a perspective view of a soft tissue attachment device in accordance with another exemplary embodiment of the present invention.
Figure 9:
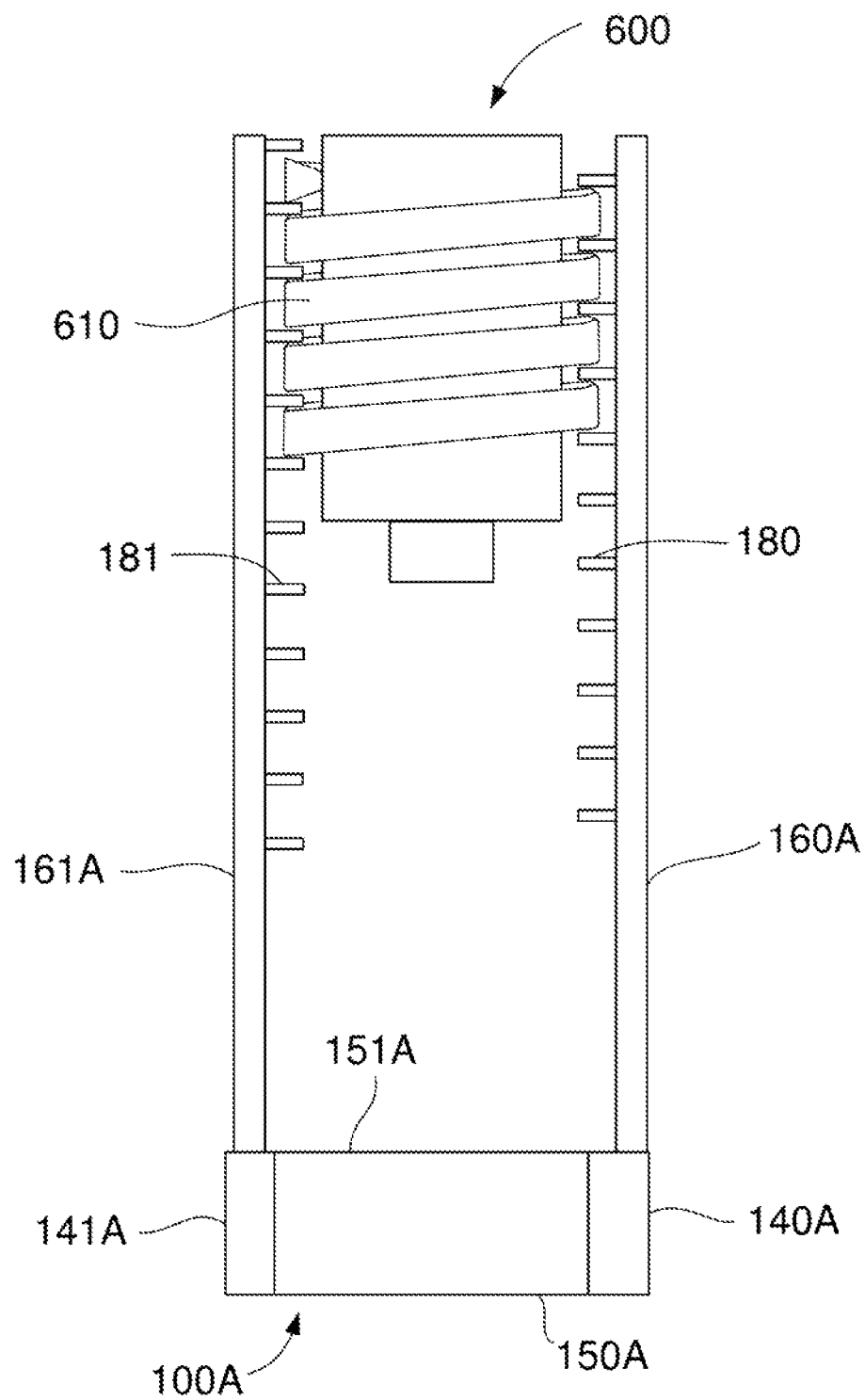
FIG. 9 is a top plan view of the soft tissue attachment device of FIG. 8.

FIGS. 8 and 9 show soft tissue attachment device 100A which includes body 101A. Body 101A includes anterior surface 150A, posterior surface 151A, lateral end 140A, and medial end 141A. Similar to device 100, device 100A includes lateral attachment post 160A extending from posterior surface 151A, proximate lateral end 140A. However, instead of including a flat surface for engagement with a lateral set screw, lateral attachment post 160A includes gear teeth 180 disposed on the medial side thereof. Device 100A also includes medial attachment post 161A which includes gear teeth 181 disposed on the lateral side thereof. Gear teeth 180, 181 are configured to engage threads 610 of worm screw 600. Worm screw 600 is preinstalled within a cylindrical chamber inside a prosthesis wherein the cylindrical chamber is in communication with attachment openings configured to receive medial and lateral attachment posts 160A and 161A. Worm screw 600 is rotated via torque applied by a tool (not shown) inserted in drive opening 620. Drive opening 620 may be any suitable shape for receiving a rotational tool therein, for example, a Philips head, flat head, star key, allen key, etc. Drive opening 620 is accessed through access opening 190 which extends from anterior surface 150A to posterior surface 151A. The prosthesis includes a corresponding access opening configured to be coaxially aligned with access opening 190 when attachment posts 160A and 161A are inserted into the attachment openings in the prosthesis.

Figure 10:
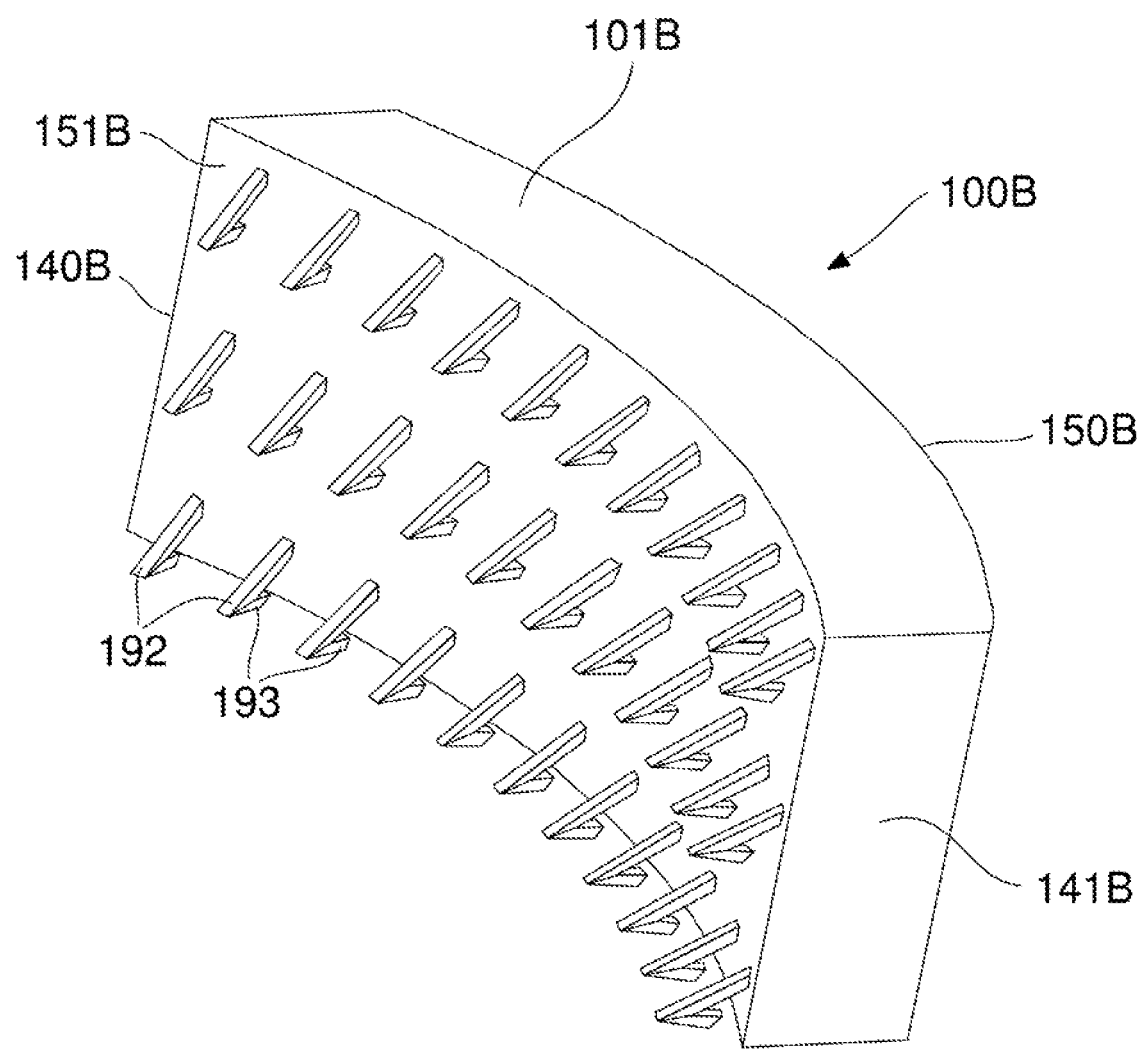
FIG. 10 is a perspective view of a soft tissue attachment device in accordance with another exemplary embodiment of the present invention.

FIG. 10 shows soft tissue attachment device 100B which includes body 101B. Body 101B includes anterior surface 150B, posterior surface 151B, lateral end 140B, and medial end 141B. These surfaces can represent any of the same surfaces on the soft tissue attachment devices mentioned in this application. Projections 192 are designed to be located on the posterior surface of the soft tissue attachment device to facilitate holding the soft tissue in place while relying on other means to affix the device to the prosthesis. Each projection 192 includes barb 193 angled back toward posterior surface 151B. Projections 192 are shorter than the thickness of the soft tissue. It should also be understood that barbs 193 should face away from the direction of pull of the soft tissue being attached. In an alternative embodiment, some or all of projections 192 could be made long enough to serve as the means of connecting device 100B to the prosthesis. In such a configuration, the longer projections 192 are longer than the thickness of the soft tissue and are configured to pass through the soft tissue and into corresponding openings on the prosthesis. Barbs 193 are configured to deflect while projections 192 pass into the corresponding openings on the prosthesis. After barbs 193 pass through the corresponding openings, barbs 193 assume their original configuration, preventing withdrawal of soft tissue attachment device 100B from the prosthesis. Soft tissue device 100B and the prosthesis may include alignment markings on the anterior surfaces 150B thereof to facilitate alignment of the projections with the corresponding openings on the prosthesis. It may be advantageous to produce devices 100B including different lengths of projections to accommodate varying soft tissue thicknesses.

Figure 11:
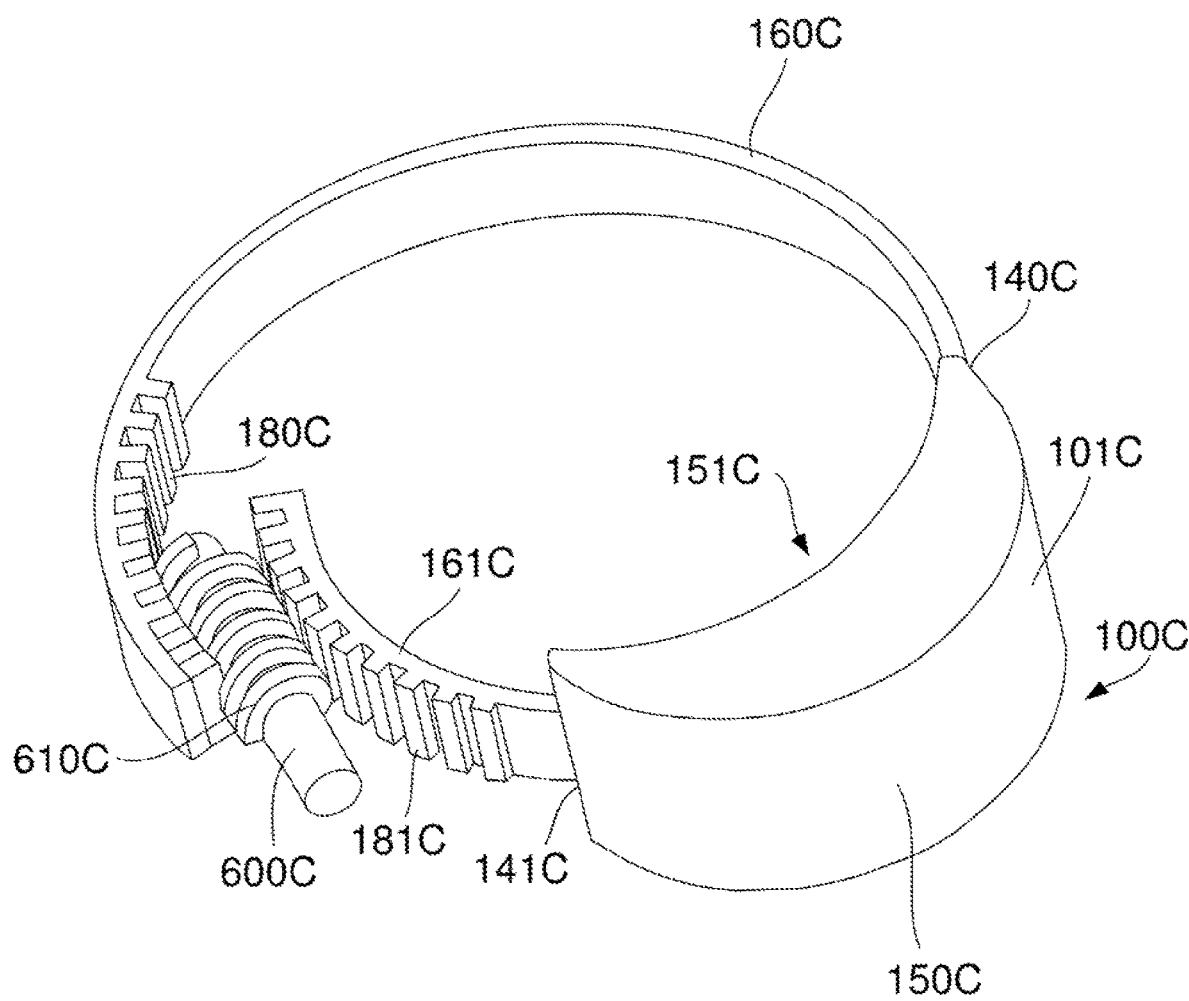
FIG. 11 is a perspective view of a soft tissue attachment device in accordance with another exemplary embodiment of the present invention.

FIG. 11 shows soft tissue attachment device 100C which includes body 101C. Body 101C includes anterior surface 150C, posterior surface 151C, lateral end 140C, and medial end 141C. Device 100C includes lateral attachment strap 160C extending from lateral end 140C and medial attachment strap 161C extending from medial end 141C. Medial attachment strap 160C includes gear teeth 180C disposed on an interior surface thereof. Gear teeth 180C are configured to engage threads 610C of worm screw 600C. Lateral attachment strap 141C includes gear teeth 181C disposed on an exterior surface thereof. Gear teeth 181C are configured to engage gear threads 610C of worm screw 600C. Worm screw 600 is preinstalled within a chamber inside a prosthesis wherein the chamber is in communication with attachment openings configured to receive medial and lateral attachment straps 160C and 161C or it may be externally contained in a housing, the entire construct wraps around the prosthesis.

Figure 12:
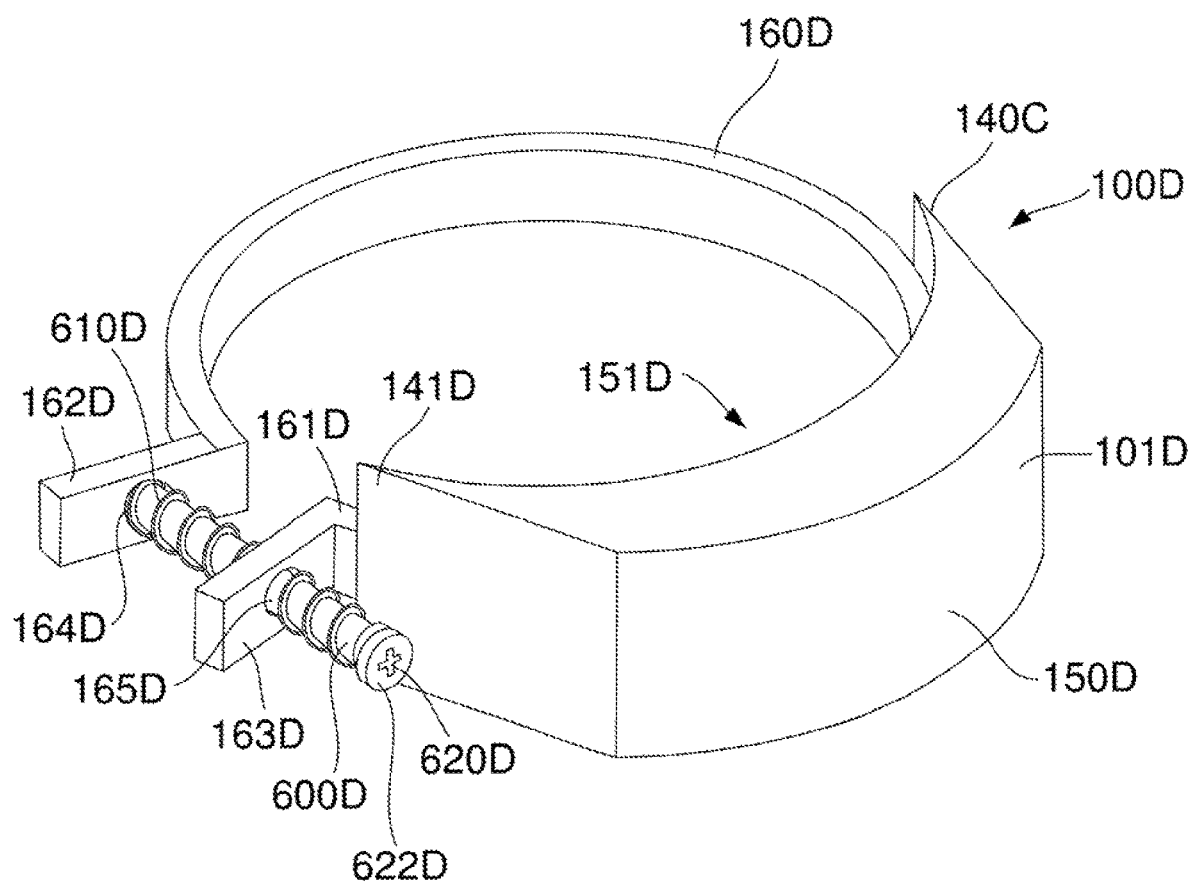
FIG. 12 is a perspective view of a soft tissue attachment device in accordance with another exemplary embodiment of the present invention.

FIG. 12 shows soft tissue attachment device 100D which includes body 101D. Body 101D includes anterior surface 150D, posterior surface 151D, lateral end 140D, and medial end 141D. Device 100D includes lateral attachment strap 160D extending from lateral end 140D and medial attachment strap 161D extending from medial end 141D. Medial attachment strap 160D includes tab 162D extending orthogonally therefrom. Tab 162D includes threaded opening 164D. Lateral attachment strap 141D includes tab 163D extending orthogonally therefrom. Tab 163D includes non-threaded opening 165D. Screw 600D is configured to be inserted through opening 165D into threaded opening 164D. Screw threads 610D are configured to cooperate with the threads of threaded opening 164D such that clockwise rotation of screw 600D causes screw 600D to linearly advance through threaded opening 164D, thereby causing screw head 622D to contact tab 163D. Continued rotation of screw 610D will apply force to tab 163 which causes posterior surface 151D to clamp down on the soft tissue. Similar to the worm screw 600, screw 600D includes drive opening 620D. Drive opening 620D may be any suitable shape for receiving a rotational tool therein, for example, a Philips head, flat head, star key, allen key, etc. Soft tissue attachment device 100D may be preinstalled in a prosthesis such that attachment straps 140D, 141D and screw are contained within the prosthesis and drive opening is accessible through an opening in the prosthesis. Alternatively, the prosthesis may have a recess surrounding the prosthesis that permits the medial and lateral straps 160D, 161D to fit therein such that the outer surfaces of the straps are flush with, if not recessed to, the out surface of the prosthesis. Soft tissue attachment device may also include a protrusion or peg disposed on the interior surface of either or both attachment straps 160D, 161D that fits into a corresponding depression on the prosthesis to aid in positioning and attachment.

Figure 13:
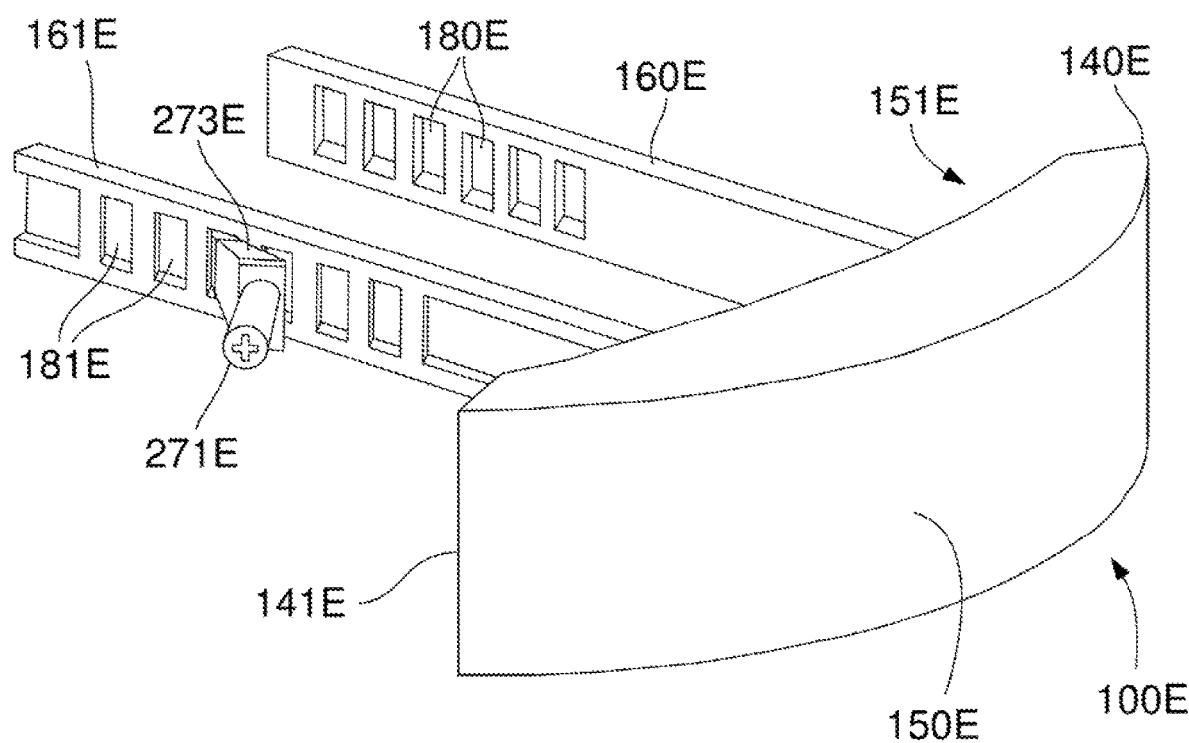
FIG. 13 is a perspective view of a soft tissue attachment device in accordance with another exemplary embodiment of the present invention.
Figure 14:
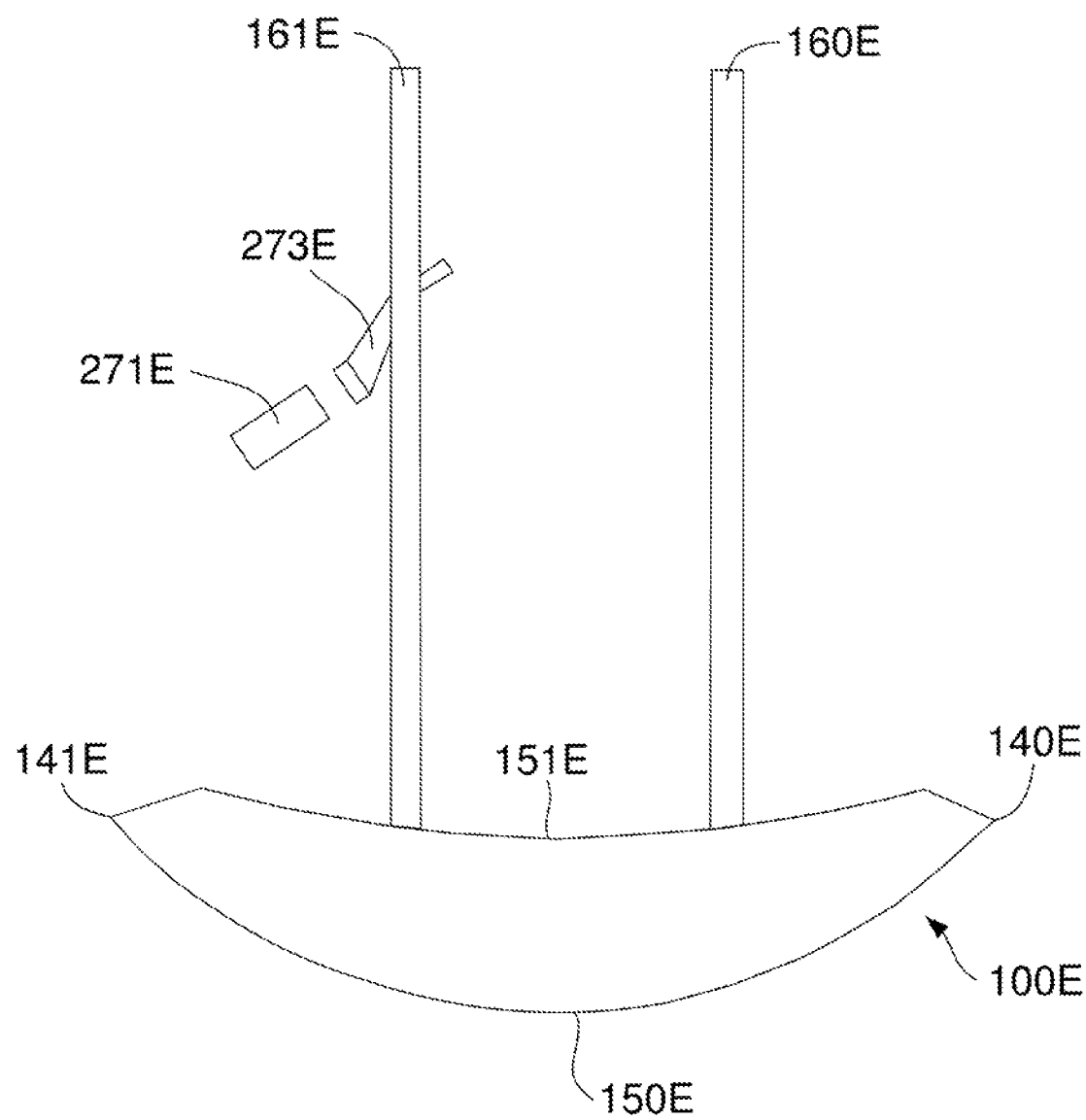
FIG. 14 is a top plan view of the soft tissue attachment device in FIG. 13.

FIGS. 13 and 14 show soft tissue attachment device 100E which includes body 101E. Body 101E includes anterior surface 150E, posterior surface 151E, lateral end 140E, and medial end 141E. Similar to device 100, device 100E includes lateral attachment post 160E extending from posterior surface 151E. However, instead of including a flat surface for engagement with a lateral set screw, lateral attachment post 160E includes a plurality of angled slots 180E extending therethrough. Device 100E also includes medial attachment post 161E which includes angled slots 181E extending therethrough. Angled slots 180E, 181E are configured to receive posts 273E therein. Post 273E is pushed into angled slot 181E by advancing screw 271E.

Figure 15:
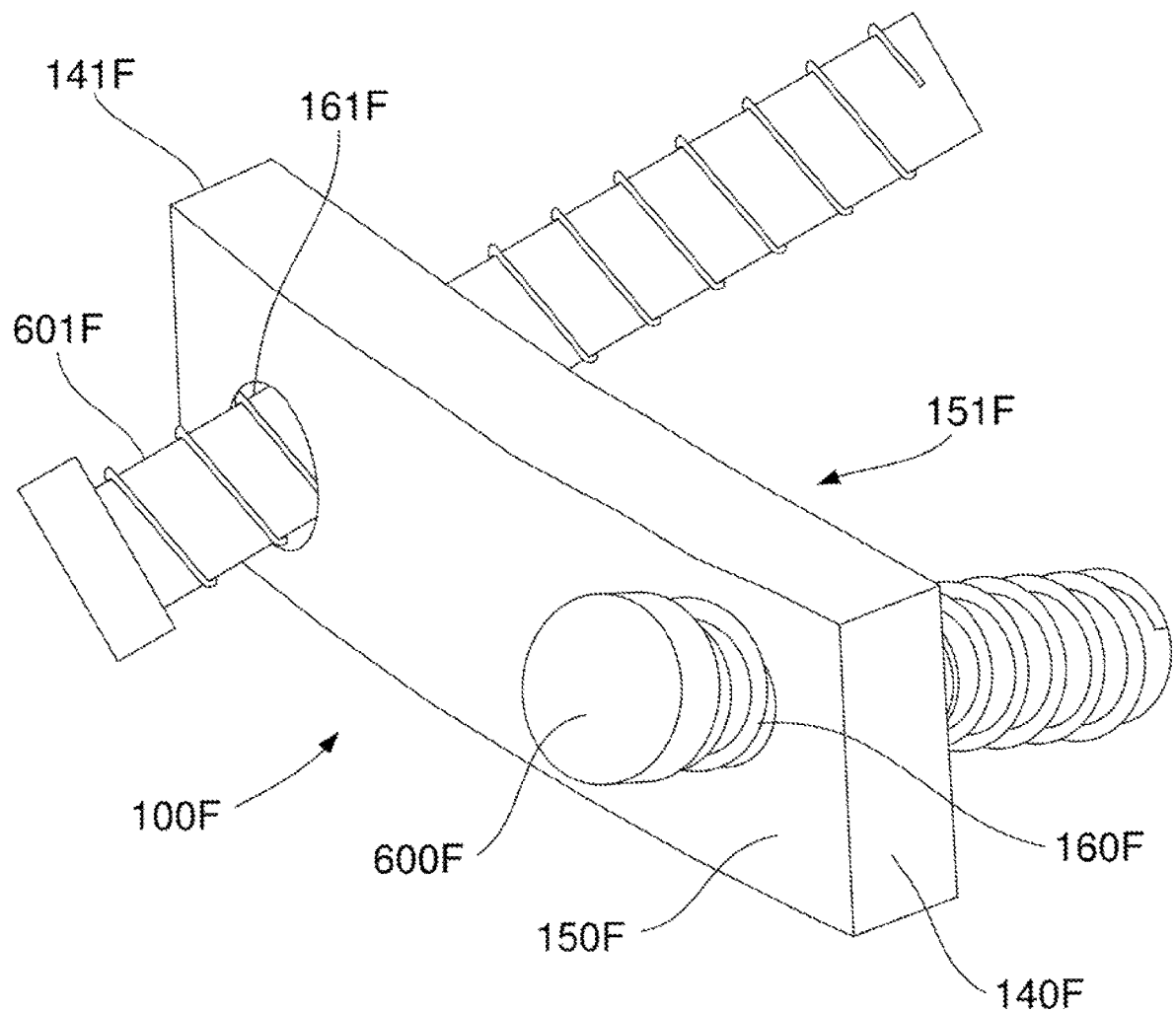
FIG. 15 is a perspective view of a soft tissue attachment device in accordance with another exemplary embodiment of the present invention.

FIG. 15 shows soft tissue attachment device 100F. Device 100F includes anterior surface 150F, posterior surface 151F, lateral end 140F, medial end 141F, lateral attachment opening 160F, and medial attachment opening 161F. Openings 160F, 161F may be configured to receive screws 600F, 601F at any angle, in which case, screws 600F, 601F may be polyaxial screws with generally spherical heads. Alternatively, openings 160F, 161F may each be configured to receive a screw at only a predetermined insertion angle. The predetermined insertion angles may be parallel, convergent, or divergent. A prosthesis for use with device 100F may include multiple threaded holes at varying angles to accommodate the introduction of screws 600F, 601F. Alternatively, the prosthesis may include rotatable apparatuses, each with a single threaded opening capable of being rotated to allow for varying insertion angles.

Figure 16:
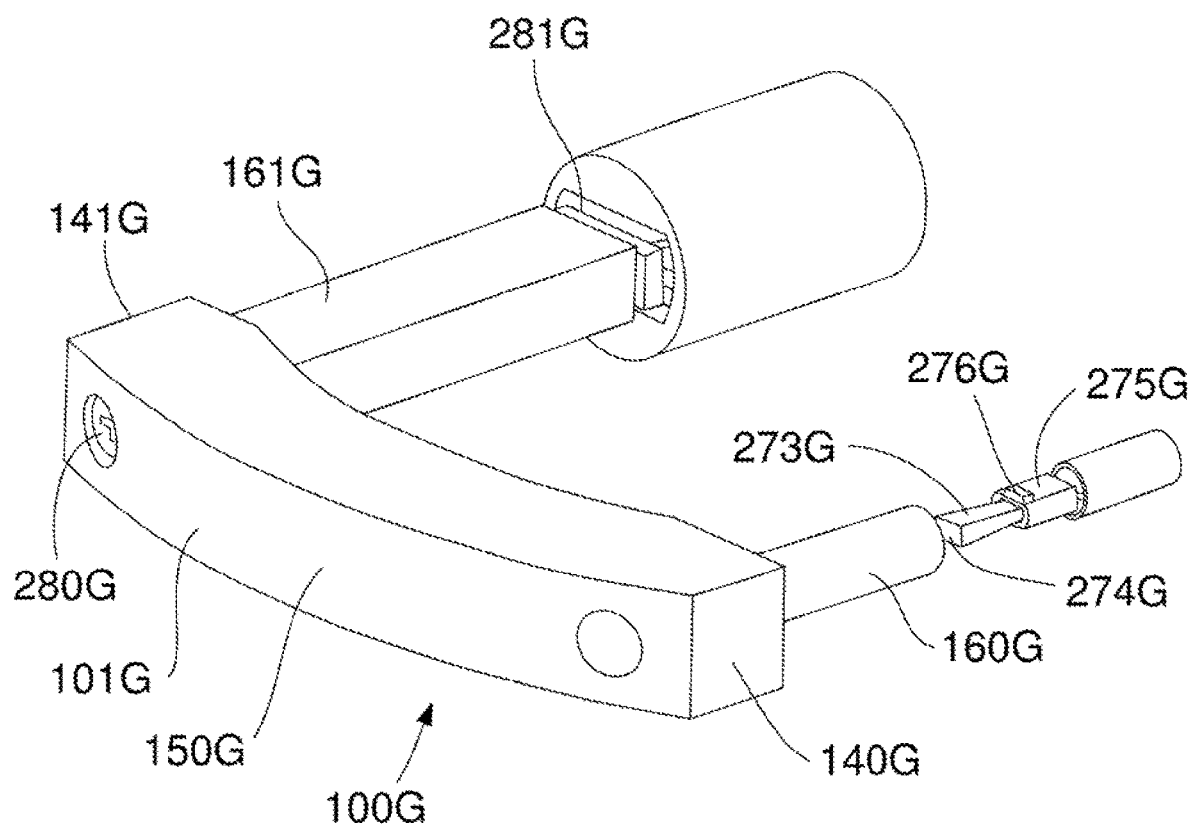
FIG. 16 is a front perspective view of a soft tissue attachment device in accordance with another exemplary embodiment of the present invention.
Figure 17:
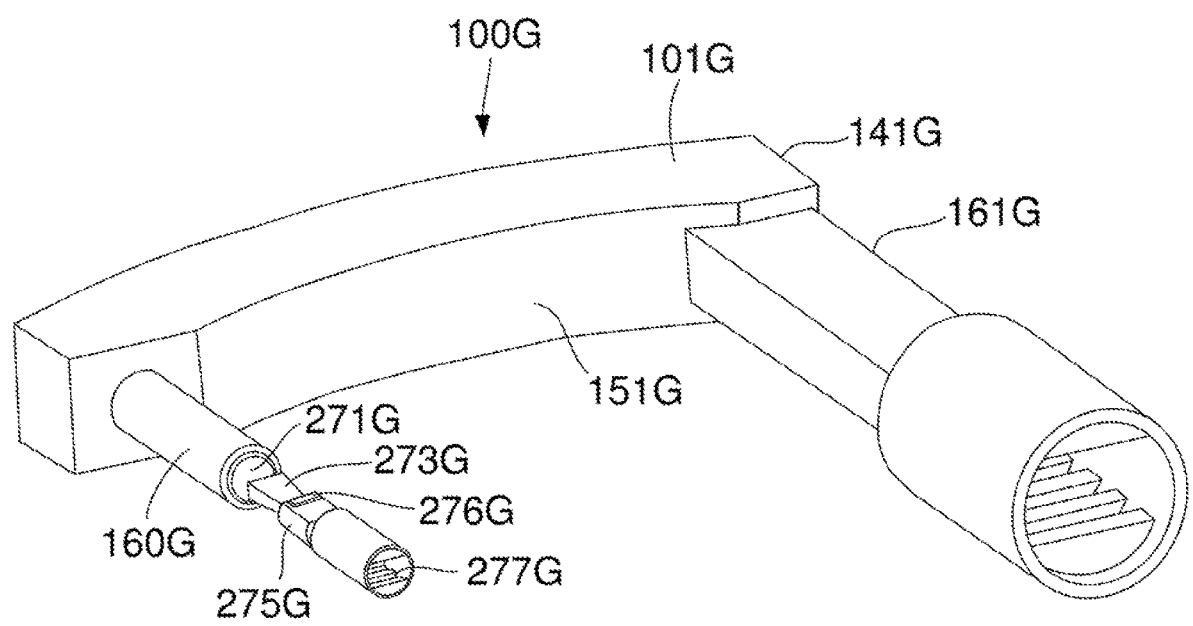
FIG. 17 is a rear perspective view of the soft tissue attachment device in FIG. 16.

FIGS. 16 and 17 show soft tissue attachment device 100G which includes body 101G. Body 101G includes anterior surface 150G, posterior surface 151G, lateral end 140G, and medial end 141G. Similar to device 100, device 100G includes lateral attachment post 160G extending from posterior surface 151G, proximate lateral end 140G. However, instead of including a flat surface for engagement with a lateral set screw, lateral attachment post 160G is a partially threaded cylinder. Within the cylinder is a screw 271G configured to engage a trailing edge 274G of a wedge 273G. Advancement of wedge 273G into box 275G (also located within lateral attachment post 160G) causes stops 276G to protrude from openings on the top and bottom of lateral attachment post 160G (not shown) and into corresponding slots 277G in the prosthesis, thereby securing the device 100G to the prosthesis. Device 100G also includes medial attachment post 161G extending from posterior surface 151G, proximate medial end 141G. Medial attachment post 161G includes a rotatable shaft 280G disposed inside. The distal end of rotatable shaft 280G includes a rectangular protrusion 281G. Rotation of rotatable shaft 280G causes rectangular protrusion 281G to engage one of corresponding slots 287G located with the prosthesis. It should be noted that both medial attachment post 161G and lateral attachment post 160G may include the structure shown and described for either of the posts 160G, 161G.

Figure 18:
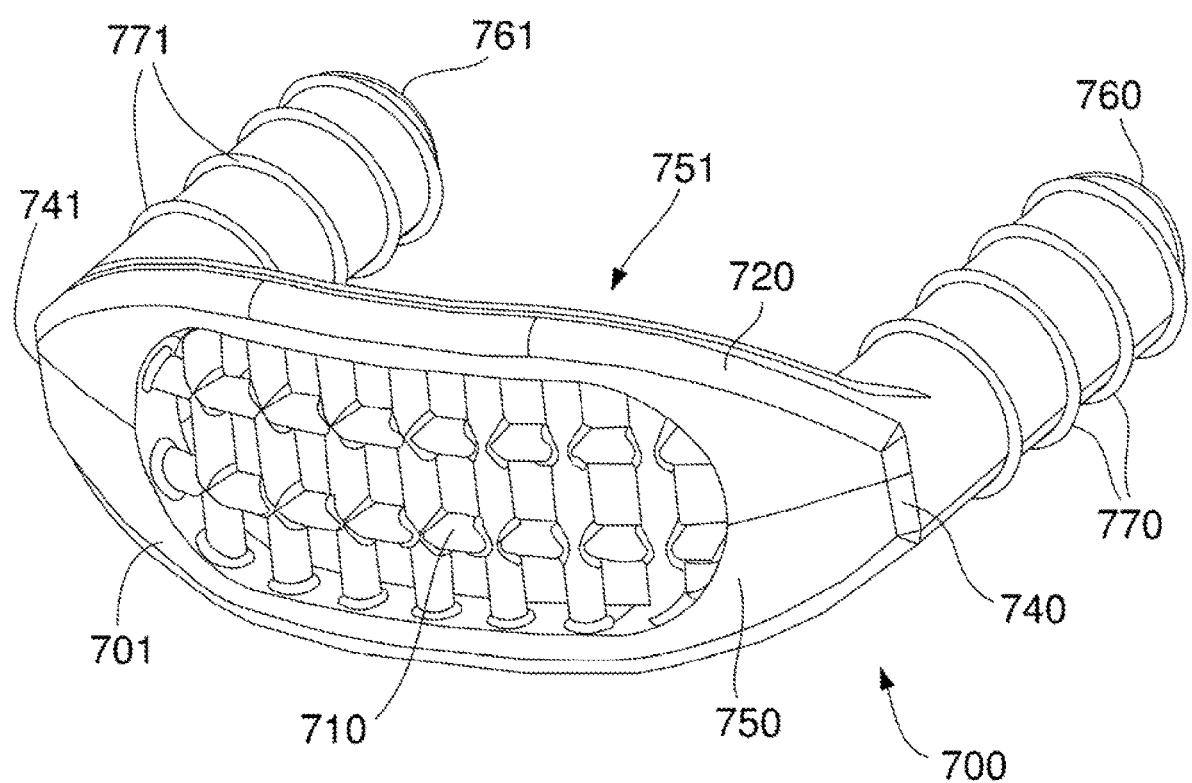
FIG. 18 is a perspective view of a soft tissue attachment device in accordance with another exemplary embodiment of the present invention.

FIG. 18 shows soft tissue attachment device 700. Device 700 is similar to device 100 save for the apparatus used to attach device 700 to a prosthesis. Similar to device 100, device 700 includes body 701 which has two parts, frame 720 and porous section 710. Body 701 of device 700 includes anterior surface 750, posterior surface 751, lateral end 740, and medial end 741. Body 701 includes lateral attachment post 770 which extends from posterior surface 751 and is located proximate lateral end 740. Lateral attachment post 760 includes a plurality of teeth 770 extending therefrom. Body 701 also includes medial attachment post 761 which extends from posterior surface 751 and is located proximate medial end 741. Medial attachment post 761 includes a plurality of teeth 771 extending therefrom. Teeth 770,771 may be ratchets. That is, they may have a gently sloping front faces that allow for linear insertion and steeply angle rear faces that prevent removal. The prosthesis preferably includes a complementary set of ratchets disposed in the openings into which attachment posts 760, 761 are to be inserted. The maximum dimension of teeth 770, 771 should be larger than the minimum diameter of the corresponding teeth inside the prosthesis. As such, teeth 770, 771 are configured to deflect slightly as each pair of teeth pass a complementary pair of teeth.

Figure 19:
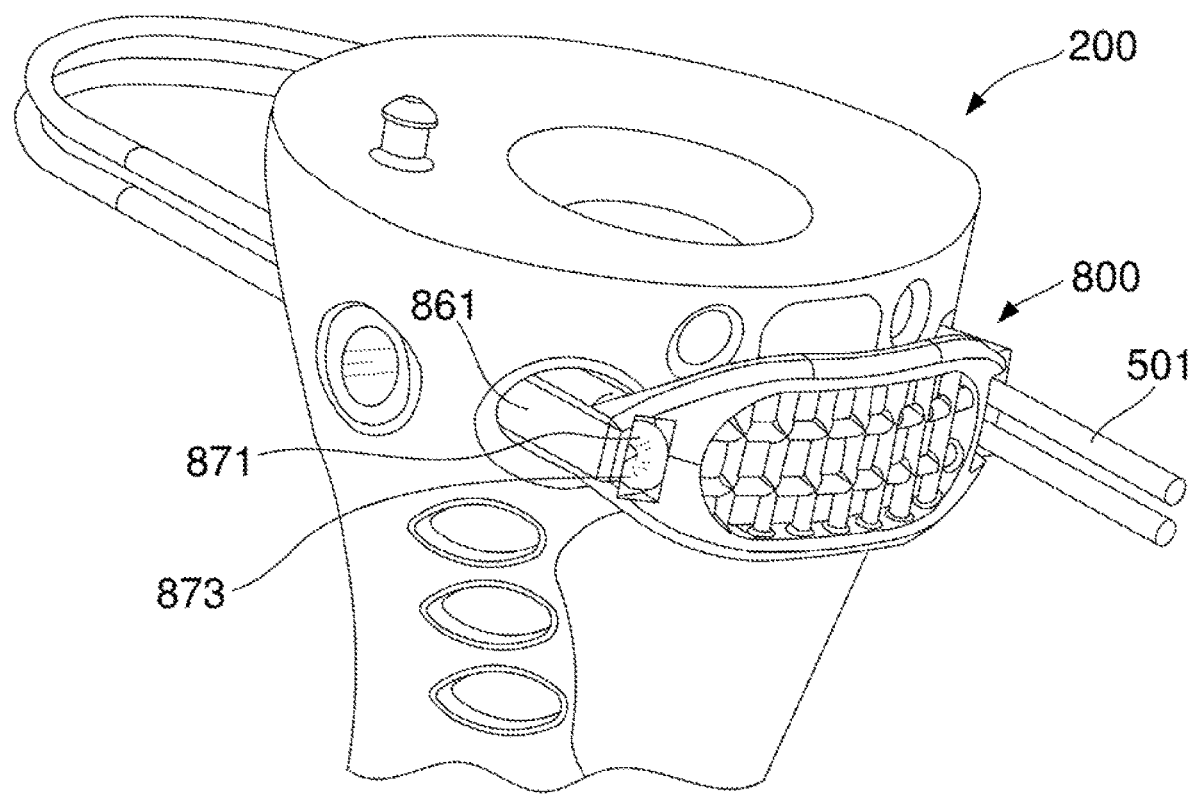
FIG. 19 is a perspective view of a soft tissue attachment device in accordance with another exemplary embodiment of the present invention.

FIG. 19 show soft tissue attachment device 800. Device 800 is similar to device 100 except for the apparatus used to attach device 800 to proximal tibial component 200. Similar to device 100, device 800 includes medial attachment post 861. However, device 800 includes medial attachment openings 871 and 873 which extend from anterior surface 850 to a posterior surface of medial attachment post 861. Device 800 also includes a lateral attachment post with lateral attachment openings extending therethrough. Attachment of device 800 is facilitated by cable 501. Cable 501 may be made of a woven polymeric material or a monofilament wire. Cable 501 may be first inserted through one of the lateral attachment openings, wrapped around the posterior of proximal tibial component 200, inserted posteriorly through medial attachment opening 871, inserted anteriorly through medial attachment opening 873, wrapped around the posterior surface of proximal tibial component 200, and inserted posteriorly through the other lateral attachment opening. In such a configuration, leading end and trailing end of cable 501 are located adjacent one another. The leading and trailing ends of cable 501 may be secured by tying them together using any type of knot sufficient for creating a permanent connection. Alternatively, the ends of cable 501 my be secured by a cable retention device (not shown) affixed to cable 501 adjacent to the lateral attachment openings.

Installation of the soft tissue attachment devices disclosed herein may be aided by a set of specialized tools (not shown) for accurately applying an appropriate amount of tension to the soft tissue attachment device to maximize grip of the tissue without causing necrosis. For example, with regard to device 100 in FIGS. 1A and 1B, a prosthesis may have anchor points where the tool temporarily anchors to the prosthesis and applies uniform pressure across anterior surface 150. The tool may include a gauge showing the amount of pressure being applied to the soft tissue. The tool may further include a dial to slowly increase the amount of force applied. Once the desired pressure is achieved, set screws are tightened against flat surfaces 170, 171 to affix device 100 to the prosthesis. Such an installation tool enables the surgeon to precisely apply the correct amount of pressure to the soft tissue without fear of creating too much pressure and preventing blood flow in the soft tissue. A similar tool would be useful for installing devices 300, 100E, 100G, 700, 800 of FIGS. 6, 13, 16, 17, 18, 19, respectively. An installation tool useful for devices 100A, 100C, 100D, and 100F would include a driver that converts the rotational force applied to the screws into the resulting pressure exerted by the device on the soft tissue.

It should be noted that any disclosed embodiment may come preinstalled on a prosthesis and merely has enough space between the posterior surface of the device and the anterior surface of the prosthesis in order to pull the soft tissue between the two surfaces.

Other embodiments of the invention will be apparent to those skilled in the art from consideration of the specification and practice of the invention disclosed herein. It is intended that the embodiments described below be considered as exemplary only, with a true scope and spirit of the invention being indicated by the appended claims. Moreover, none of the features disclosed in this specification should be construed as essential elements, and therefore, no disclosed features should be construed as being part of the claimed invention unless the features are specifically recited in the claims. In addition, it should be understood that any of the features disclosed on any particular embodiment may be incorporated in whole or in part on any of the other disclosed embodiments.

We claim:

1. A soft tissue fixation device comprising:
 a body having
  an anterior surface;
  a posterior surface that is adapted to cooperate with a surface of a prosthetic implant;
  a depth extending between the anterior surface and the posterior surface;
  the body bounded, at least in part, by a frame;
  a porous section disposed within the frame, wherein the porous section extends through the depth of the body; and
  at least one attachment opening in the body; and
 a cable having a shaped end that is configured to bias against the at least one attachment opening to attach the cable to the body and enable using the cable to attach the body to the prosthetic implant.

2. The device of claim 1, wherein the posterior surface further comprises a friction enhancing surface configured to engage soft tissue.

3. The device of claim 2, wherein the friction enhancing surface comprises projections.

4. The device of claim 1, wherein the at least one attachment opening is located in the frame of the body.

5. The device of claim 1, wherein the frame further comprises a solid perimeter.

6. The device of claim 1, wherein the cable circumscribes the prosthetic implant, and wherein the cable engages the prosthetic implant and a second attachment opening in the body of the fixation device to facilitate fixing the body to the prosthetic implant.

7. The device of claim 6, wherein the first and second attachment openings are located in the frame of the body.

8. The device of claim 6, further comprising a cable retention device configured to be attached to the cable to prevent passage of the cable through the second attachment opening.

9. The device of claim 1, wherein the frame and the porous section are different materials.

10. The device of claim 1, wherein the porous section comprises a lattice.

11. The device of claim 10, wherein the lattice is comprised of generally vertical and horizontal strips.

12. The device of claim 1, wherein the porous section generally includes a pore size of about 500-700 microns.

13. A soft tissue fixation device comprising:
a body having
an anterior surface;
a posterior surface that is adapted to cooperate with a surface of a prosthetic implant, the posterior surface includes projections configured to engage soft tissue;
a depth extending between the anterior surface and the posterior surface;
the body bounded, at least in part, by a frame;
a porous section disposed within the frame, wherein the porous section extends through the depth of the body; and
at least one attachment opening in the body; and
a cable having a shaped end that is configured to bias against the at least one attachment opening to attach the cable to the body and enable using the cable to attach the body to the prosthetic implant.

14. The device of claim 13, wherein the cable circumscribes the prosthetic implant, and wherein the cable engages the prosthetic implant and a second attachment opening in the body of the fixation device to facilitate fixing the body to the prosthetic implant.

15. The device of claim 14, wherein the first and second attachment openings are located in the frame of the body.

16. The device of claim 14, further comprising a cable retention device configured to be attached to the cable to prevent passage of the cable through the second attachment opening.

17. The device of claim 13, wherein the porous section comprises a lattice.

18. The device of claim 17, wherein the lattice is comprised of generally vertical and horizontal strips.

19. The device of claim 13, wherein the frame and the porous section are different materials.

20. A soft tissue fixation device comprising:
a body having
an anterior surface;
a posterior surface that is adapted to cooperate with a surface of a prosthetic implant, the posterior surface includes projections configured to engage soft tissue;
a depth extending between the anterior surface and the posterior surface;
the body bounded, at least in part, by a frame;
a porous section disposed within the frame, wherein the porous section extends through the depth of the body; and
two attachment openings located in the frame of the body;
a cable having a shaped first end that is configured to bias against one of the two attachment openings to attach the cable to the body and enable using the cable to attach the body to the prosthetic implant, wherein the cable circumscribes the prosthetic implant, and wherein a second end of the cable interacts with the other of the two attachment openings in the body of the fixation device to facilitate fixing the body to the prosthetic implant.

* * * * *